United States Patent
Al-Khattaf et al.

(10) Patent No.: US 10,035,140 B2
(45) Date of Patent: Jul. 31, 2018

(54) PROCESS FOR PRODUCING XYLENE USING A METAL-DOPED ZEOLITE CATALYST

(71) Applicant: KING FAHD UNIVERSITY OF PETROLEUM AND MINERALS, Dhahran (SA)

(72) Inventors: Sulaiman Saleh Al-Khattaf, Dhahran (SA); Syed Ahmed Ali, Dhahran (SA); Abdullah Mohammed Aitani, Dhahran (SA)

(73) Assignee: King Fahd University of Petroleum and Minerals, Dhahran (SA)

( * ) Notice: Subject to any disclaimer, the term of this patent is extended or adjusted under 35 U.S.C. 154(b) by 0 days.

(21) Appl. No.: 15/270,179

(22) Filed: Sep. 20, 2016

(65) Prior Publication Data
US 2018/0078929 A1 Mar. 22, 2018

(51) Int. Cl.
C07C 6/06 (2006.01)
C07C 4/18 (2006.01)
B01J 29/78 (2006.01)

(52) U.S. Cl.
CPC ........ B01J 29/7876 (2013.01); B01J 29/78 (2013.01); C07C 6/06 (2013.01); C07C 2529/78 (2013.01)

(58) Field of Classification Search
None
See application file for complete search history.

(56) References Cited

U.S. PATENT DOCUMENTS

| | | | |
|---|---|---|---|
| 5,030,787 A | 7/1991 | Absil et al. | |
| 5,847,256 A | 12/1998 | Ichioka et al. | |
| 5,866,742 A * | 2/1999 | Wu | C07C 6/126 585/475 |
| 6,297,417 B1 * | 10/2001 | Samson | C07C 2/66 585/448 |
| 8,481,443 B2 | 7/2013 | Levin et al. | |
| 9,018,121 B2 | 4/2015 | Ross et al. | |
| 2005/0143614 A1 | 6/2005 | Leon-Escamilla et al. | |
| 2009/0112034 A1 * | 4/2009 | Levin | C07C 6/126 585/475 |

(Continued)

FOREIGN PATENT DOCUMENTS

| | | |
|---|---|---|
| IN | 268319 B | 10/2011 |
| KR | 10-1359973 13 | 2/2014 |

OTHER PUBLICATIONS

Sulaiman S. Al-Khattaf, et al., "Catalysis of metal supported zeolites for dealkylation-transalkylation of alkyl-aromatics", Applied Catalysis A: General, vol. 514, 2016, pp. 154-163.

(Continued)

*Primary Examiner* — Philip Y Louie
(74) *Attorney, Agent, or Firm* — Oblon, McClelland, Maier & Neustadt, L.L.P.

(57) ABSTRACT

A method of preparing a metal-doped zeolite catalyst with a modified topology (e.g. a pillared zeolite or a delaminated zeolite), and a method of using thereof in a process for converting an alkyl-aromatic hydrocarbon stream to BTX (benzene/toluene/xylene), wherein an enhanced pore topology in the metal-doped zeolite catalyst determines a selectivity to transalkylation of trimethylbenzene to xylene, which in turn leads to a higher xylene yield. Various embodiments of the method of preparing the metal-doped zeolite catalyst, and the process for converting the alkyl-aromatic hydrocarbon stream to BTX are also provided.

9 Claims, 4 Drawing Sheets

(56) References Cited

U.S. PATENT DOCUMENTS

2013/0165727 A1* 6/2013 Baeck .................. C07C 5/2775
585/489
2016/0176787 A1* 6/2016 Molinier ................ C07C 6/126
585/475

OTHER PUBLICATIONS

José M. Serra, et al., "Optimizing the conversion of heavy reformate streams into xylenes with zeolite catalysts by using knowledge base high-throughput experimentation techniques", Journal of Catalysis, vol. 232, 2005, pp. 342-354.

José M. Serra, et al., "A rational design of alkyl-aromatics dealkylation—transalkylation catalysts using $C_8$ and $C_9$ alkyl-aromatics as reactants", Journal of Catalysis, vol. 227, 2004, pp. 459-469.

Jens Weitkamp, "Zeolites and catalysis", Solid State Ionics, vol. 131, 2000, pp. 175-188.

Tseng-Chang Tsai, et al., "Disproportionation Mechanism Study of Probing by n-Propylbenzene", Journal of Catalysis, vol. 133, 1992, pp. 136-145.

Se-Young Kim, et al., "Structural Evolution of B-MCM-36 and B-ITQ-2 from B-MCM-22", Bull. Korean Chem. Soc., vol. 27, No. 10, 2006, pp. 1693-1696.

Nazi Rahimi, et al., "Catalytic cracking of hydrocarbons over modified ZSM-5 zeolites to produce light olefins: A review", Applied Catalysis A: General, vol. 398, 2011, pp. 1-17.

Wu, P., et al., "Synthesis of Ti-MWW Zeolite", Springer, Synthesis, Structural Modification and Catalytic Applications to Green Oxidations, vol. VIII, 2013, 27 pages.

\* cited by examiner

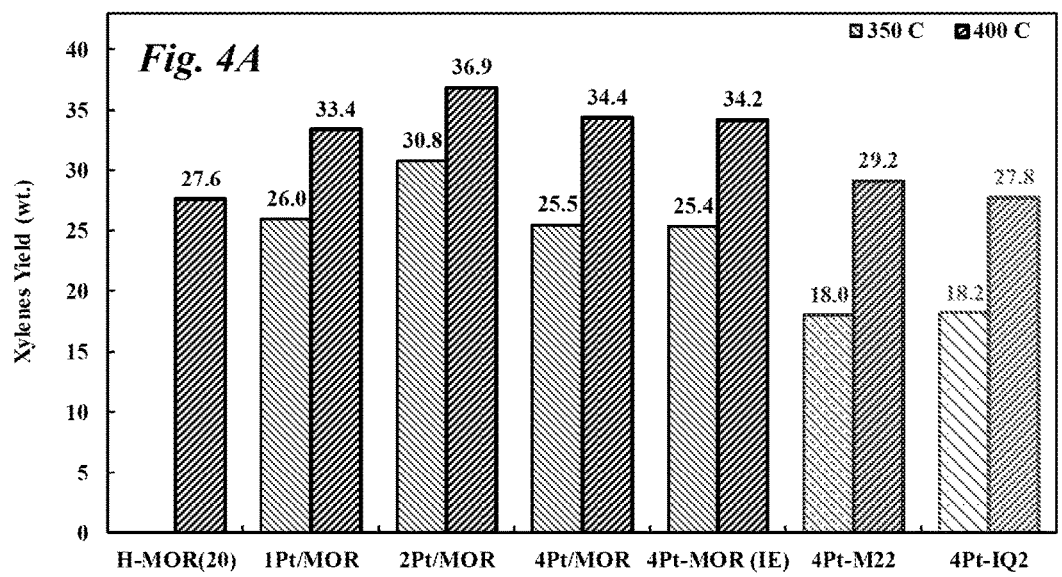
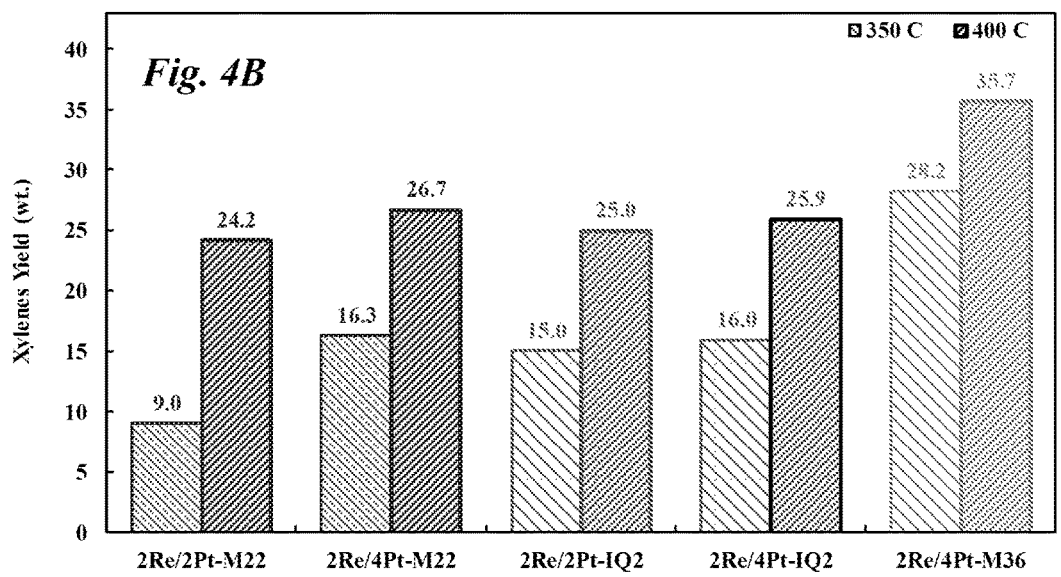

PROCESS FOR PRODUCING XYLENE USING A METAL-DOPED ZEOLITE CATALYST

BACKGROUND OF THE INVENTION

Technical Field

The present invention relates to a method of preparing a metal-doped zeolite catalyst with a modified topology (e.g. a pillared zeolite or a delaminated zeolite), and a process for converting an alkyl-aromatic hydrocarbon stream to BTX (benzene/toluene/xylene) using the metal-doped zeolite catalyst.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Mandatory regulations limiting aromatic content in gasoline are the driving force to explore alternative routes for utilizing heavy aromatics produced from catalytic reforming of naphtha. One economically viable option is to convert the heavy reformate stream, which is rich in heavy aromatics (mainly $C_{9+}$ aromatic compounds), to xylenes [T. C. Tsai, S. B. Liu, I. Wang, Catal. Surv. Asia 13 (2009) 94-103]. The conversion process, catalyzed by zeolites, comprises transalkylation and disproportionation reactions via a bimolecular reaction intermediate (biphenyl methane carbenium ion intermediate). Scission of ethyl and propyl side chains (dealkylation) from $C_9+$ aromatics are important routes leading to the formation of xylenes [S. Ali, M. Ali, K. Al-Nawad, C. Ercan, Y. Wang, Appl. Catal., A. 393 (1-2) 96-108; T. C. Tsai, 1. Wang J. Catal. 133 (1992) 136-145; J. Das, Y. S. Bhat, A. B. Halgeri, Catal. Lett. 23 (1994) 161-168].

Research studies on transalkylation reactions over different zeolites with or without incorporation of metals have been reported in the literature. Use of various medium-pore zeolites such as ZSM-5 [S. A. Ali, K. Ogunronbi, S. Al-Khattaf, Chem. Engg. Res. Des., 91 (2013) 2601-2616], NU-87 [S. Park, H. Rhee, Catal. Today 63 (2000) 267-273], and MCM-22 [S. Park, H. Rhee, Catal. Today 63 (2000) 267-273], as well as large-pore zeolites such as ZSM-12 [T. C. Tsai, S. Liu, I. Wang, Appl. Catal. A: Gen. 181 (1999) 355-398; T. C. Tsai, W. H. Chen, S. B. Liu, C. H. Tsai, I. Wang, Catal. Today 73 (2002) 39-47], faujasites [I. Wang, T. C. Tsai, S. T. Huang, Ind. Eng. Chem. Res., 29 (1990) 2005-2012; J. A. Atias, G. Tonetto, H. de Lasa, Ind. Eng. Chem. Res., 42 (2003) 4162-4173; S. Al-Khattaf, N. Tukur, A. Al-Amer, Ind. Eng. Chem. Res., 46 (2007) 4459-4467; A. Krejci, S. Al-Khattaf, M. Ali, M. Bejblova, J. Cejka, Appl. Catal. 377 (2010) 99-106], zeolite β [S. Park, H. Rhee, Catal. Today 63 (2000) 267-273; J. Das, Y. Bhat, A. Halgeri, Appl. Catal., 116 (1994) 71-79; A. Halgeri, J. Das, Appl. Catal. A: Gen., 181 (1999) 347-354], mordenite [J. A. Atias, G. Tonetto, H. de Lasa, Ind. Eng. Chem. Res., 42 (2003) 4162-4173; A. Krejci, S. Al-Khattaf, M. Ali, M. Bejblova, J. Cejka, Appl. Catal. 377 (2010) 99-106; J. Cejka, J. Kotrla, A. Krejci, Appl. Catal. A: Gen., 277 (2004) 191-199], and zeolite L [J. Cejka, J. Kotrla, A. Krejci, Appl. Catal. A: Gen., 277 (2004) 191-199], have been reported. These studies show that the dealkylation and transalkylation of $C_{9+}$ aromatics are significantly influenced by the topology of the pore structure as well as the type and strength of acid sites of the zeolite catalysts. [J. M. Serra, E. Guillon, A. Corma, J. Catal. 232 (2005) 342-354].

Hydrogenation functionality may also be introduced to a zeolitic catalyst by incorporating suitable metals. Such bifunctional catalysts promote desirable reactions such as hydrogenation of coke precursors, dealkylation, saturation of cracking products, and their subsequent alkylation [T. C. Tsai, P. Chao, W. Zeng, S. Tsai, Stud. Surf. Sci. Catal., 170B (2007) 1611-1616]. Incorporation of different metals over mordenite include Pd [G. Nacamuli, R. Vogel, S. Zones, U.S. Pat. No. 5,952,536 (1999), to Chevron Chem], Re [F. Alario, E. Benazzi, U.S. Pat. No. 6,037,512 (2000), to IFP; F. Raatz, P. Dufresne, C. Marcilly, U.S. Pat. No. 4,723,048 (1998), to IFP; U.S. Pat. No. 6,096,938], Ag, Bi, Cu, Pb [W. Cheng, D. Kong, D. Yang, H. Li, Z. Zhu, U.S. Pat. No. 6,500,997 (2002), to China Petro-Chemical Corporation], Cr, W, Co [U.S. Pat. No. 5,847,256]. Serra et al. [J. M. Serra, E. Guillon, A. Corma, J. Catal. 232 (2005) 342-354] studied the conversion of heavy reformate with toluene over seven zeolites and each zeolite was impregnated with one or more metals including Re, Ni, Mo, Ga, Pt, La, and Bi. The incorporation of certain metals, such as Mo and Re, was shown to increase the xylene yield.

The process of producing xylene from a $C_{9+}$ aromatic feedstock through dealkylation, transalkylation, and/or disproportionation in the presence of a zeolite catalyst is widely investigated. For example, the U.S. Pat. No. 5,847,256A, the U.S. Pat. No. 8,481,443B2, and the U.S. Pat. No. 5,030,787A references disclose a process of converting a feedstock containing $C_{9+}$ aromatic compounds to a product containing $C_6$-$C_8$ aromatic compounds by contacting the feedstock with a zeolite catalyst, wherein the zeolite catalyst is doped with a transition metal such as platinum. Additionally, the US20050143614A1 reference discloses an isomerization process for producing para-xylene from a feed mixture of xylene and ethylbenzene by contacting the feed mixture with a MTW-type zeolite catalyst. Furthermore, a catalyst system is disclosed in the U.S. Pat. No. 9,018,121B2, wherein the catalyst system involves two beds each contains a bimetallic zeolite catalyst (ZSM-5), and the metals being selected from Pt, Re, Ag, Cu, In, Sn, and Ru.

Although catalytic reactions (i.e. dealkylation, transalkylation, and disproportionation) of $C_9+$ aromatic hydrocarbon compounds in the presence of a metal-doped zeolite catalyst are widely understood, there has been limited research on the effect of a metal-doped zeolite catalyst with a modified topology (e.g. pillared or delaminated) on dealkylation, transalkylation, and/or disproportionation of $C_{9+}$ aromatic hydrocarbon compounds, and to convert the $C_{9+}$ alkyl-aromatic compounds to xylene.

In view of the forgoing, one objective of the present invention is provide a method of preparing a metal-doped zeolite catalyst with a modified topology, and a process for converting an alkyl-aromatic hydrocarbon stream to BTX (benzene/toluene/xylene) using the metal-doped zeolite catalyst.

BRIEF SUMMARY OF THE INVENTION

According to a first aspect the present disclosure relates to a process for converting an alkyl-aromatic hydrocarbon stream to a BTX-rich stream, involving i) contacting the alkyl-aromatic hydrocarbon stream with a zeolite catalyst in the presence of hydrogen gas in a temperature range of 200-500° C. and a pressure range of 1-3 MPa to form a product stream, wherein a molar ratio of the hydrogen gas to hydrocarbon compounds in the alkyl-aromatic hydrocarbon stream is in the range of 1:1-6:1, and wherein the zeolite catalyst includes a) a pillared MWW zeolite, and b) at least two metals selected from the group consisting of Pt, Re, Mo, and Ni, ii) separating $C_{5-}$ and $C_{9+}$ hydrocarbon compounds from the product stream to form the BTX-rich stream.

In one embodiment, the process further involves treating the zeolite catalyst with the hydrogen gas in a temperature range of 250-450° C. prior to the contacting.

In one embodiment, at least 50% by weight of the BTX-rich stream is xylene and the process further involves separating xylene from the BTX-rich stream.

In one embodiment, the alkyl-aromatic hydrocarbon stream comprises $C_{9+}$ alkyl-aromatic hydrocarbon compounds.

In one embodiment, the alkyl-aromatic hydrocarbon stream has a space velocity in the range of 1-5 $h^{-1}$.

In one embodiment, the alkyl-aromatic hydrocarbon stream comprises toluene and one or more of methylethylbenzene, trimethylbenzene, dimethylethylbenzene, tetramethylbenzene, and the process further comprises reducing a toluene content of the alkyl-aromatic hydrocarbon stream in a separation unit prior to the contacting.

In one embodiment, the alkyl-aromatic hydrocarbon stream has an average methyl-to-benzene molar ratio in the range of 2-2.5 prior to the contacting.

In one embodiment, the zeolite catalyst comprises 0.1-1 wt % Pt and 0.1-1 wt % Re.

In one embodiment, the zeolite catalyst comprises micropores having a specific pore volume in the range of 0.05-0.1 $cm^3/g$, and meso-pores having a specific pore volume in the range of 0.3-0.5 $cm^3/g$.

In one embodiment, the pillared MWW zeolite comprises silica pillars.

According to a second aspect the present disclosure relates to a process for converting an alkyl-aromatic hydrocarbon stream to a BTX-rich stream, involving i) contacting the alkyl-aromatic hydrocarbon stream with a zeolite catalyst in the presence of hydrogen gas in a temperature range of 200-500° C. and a pressure range of 1-3 MPa to form a product stream, wherein a molar ratio of the hydrogen gas to hydrocarbon compounds in the alkyl-aromatic hydrocarbon stream is in the range of 1:1-6:1, and wherein the zeolite catalyst includes a) a delaminated MWW zeolite, and b) at least two metals selected from the group consisting of Pt, Re, Mo, and Ni, ii) separating $C_{5-}$ and $C_{9+}$ hydrocarbon compounds from the product stream to form the BTX-rich stream.

In one embodiment, the zeolite catalyst includes micropores having a specific pore volume in the range of 0.03-0.07 $cm^3/g$, and meso-pores having a specific pore volume in the range of 0.7-0.75 $cm^3/g$.

According to a third aspect the present disclosure relates to a method of preparing a metal-doped pillared zeolite catalyst, involving i) treating a MWW zeolite with an ammonium halide solution in a temperature range of 50-120° C. to form an intercalated MCM-22 zeolite, ii) treating the intercalated MCM-22 zeolite with a silicate solution in a temperature range of 50-120° C. to form a pillared MCM-22 zeolite, iii) treating the pillared MCM-22 zeolite with an ammonium nitrate solution in a temperature range of 50-120° C., followed by calcining the pillared MCM-22 zeolite at a temperature in the range of 400-600° C. to form a (X,H)MCM-36 zeolite, wherein X is an alkali metal, iv) treating the (X,H)MCM-36 zeolite with the ammonium halide solution in a temperature range of 50-120° C., followed by calcining the (X,H)MCM-36 zeolite in a temperature range of 400-600° C. to form a H-MCM-36 zeolite, v) treating the H-MCM-36 zeolite with a platinum solution in a temperature range of 50-120° C. to form a Pt-MCM-36 zeolite with 0.1-1 wt % Pt.

In one embodiment, the method further involves i) oxidizing the Pt-MCM-36 zeolite in a temperature range of 100-500° C., ii) reducing the Pt-MCM-36 zeolite with a hydrogen gas, iii) treating the Pt-MCM-36 zeolite with a rhenium solution and calcining in a temperature range of 400-600° C. to form a Re/Pt-MCM-36 zeolite with 0.1-1 wt % Re.

In one embodiment, the method further involves drying the Pt-MCM-36 zeolite in an inert atmosphere in a temperature range of 300-400° C. prior to the reducing.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein:

FIG. 4A represents xylene yield at 350° C. and 400° C. in the presence of a platinum-doped mordenite (Pt/MOR), a platinum-doped MWW zeolite (Pt-M22), and a platinum-doped delaminated MWW zeolite (Pt-IQ2).

FIG. 4B represents xylene yield at 350° C. and 400° C. in the presence of a rhenium/platinum-doped MWW zeolite (Re/Pt-M22), a rhenium/platinum-doped delaminated MWW zeolite (Re/Pt-IQ2), and a rhenium/platinum-doped pillared MWW zeolite (Re/Pt-M36).

DETAILED DESCRIPTION OF THE EMBODIMENTS

Figure 1:
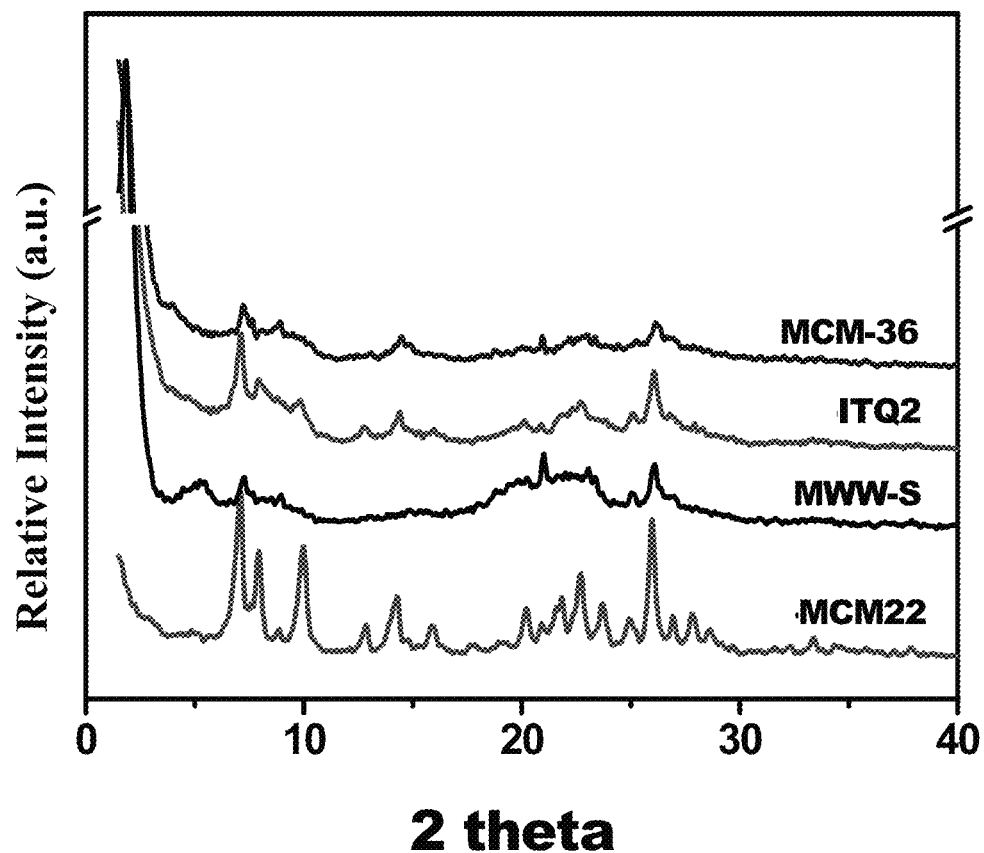
FIG. 1 represents X-ray diffractograms of a MWW zeolite (MCM-22), an intercalated MWW zeolite (MWW-S), a pillared MWW zeolite (MCM-36), and a delaminated MWW zeolite (ITQ-2).

According to a first aspect the present disclosure relates to a process for converting an alkyl-aromatic hydrocarbon stream to a BTX-rich stream, involving contacting the alkyl-aromatic hydrocarbon stream with a zeolite catalyst in the presence of hydrogen gas.

In one preferred embodiment, the alkyl-aromatic hydrocarbon stream comprises at least 80 wt %, preferably at least 85 wt %, more preferably at least 90 wt % of $C_{9}+$ alkyl-aromatic hydrocarbon compounds, and less than 20 wt %, preferably less than 15 wt %, more preferably less than 10 wt % of $C_{9-}$ alkyl-aromatic hydrocarbon compounds. Accordingly, the alkyl-aromatic hydrocarbon stream comprises toluene, benzene, xylene, ethylbenzene, methylethylbenzene, diethylbenzene, isomers of trimethylbenzene (e.g. 1,3,5-trimethylbenzene or 1,2,4-trimethylbenzene), dimethylethylbenzene, isomers of tetramethylbenzene (e.g. 1,2,4,5-tetramethylbenzene), cumene (isopropylbenzene), pseudocumene, propyl-substituted benzenes, and butyl-substituted benzenes. Suitable sources of the alkyl-aromatic hydrocarbon stream may include any $C_{9+}$ fraction from a refining, a cracking (catalytic cracking) and/or a reforming process (e.g. catalytic reforming) that is rich in aromatics. For example, the alkyl-aromatic hydrocarbon stream may be an effluent of a naphtha reformer, a fluid catalytic cracker, a steam cracker, a separation column, or a combination thereof.

Contacting as used herein refers to a process whereby a liquid-state, preferably a vaporized-state of the alkyl-aromatic hydrocarbon stream is directly contacted with a catalyst present in a catalyst bed of a reactor at reaction conditions that are favored for catalytic reactions to take place. The alkyl-aromatic hydrocarbon stream may be contacted with the catalyst by passing through the catalyst or by passing over the catalyst (e.g. a vaporized-state of the alkyl-aromatic hydrocarbon stream as an atmosphere to the catalyst). Additionally, the alkyl-aromatic hydrocarbon stream may be contacted with the catalyst by mixing the alkyl-aromatic hydrocarbon stream and the catalyst as a heterogeneous solution. Among these, the preferred contacting is by passing the alkyl-aromatic hydrocarbon stream through the catalyst.

The catalyst bed as used herein refers to a container with an internal cavity that is filled with the zeolite catalyst. Examples of the catalyst beds include, but are not limited to a hollow tube, a pipe, a duct, etc. The reactor may preferably be a cylindrical vessel with the catalyst bed located inside, wherein the alkyl-aromatic hydrocarbon stream and the hydrogen gas are contacted with the zeolite catalyst present in the catalyst bed. The reactor may include one or more catalyst beds that are located in series. In a preferred embodiment, the reactor has only one catalyst bed. The reactor may have various geometries including spherical, conical, pyramidal, rectangular, or cubical geometries. In one embodiment, the reactor has a volume of less than 1 ml, preferably less than 500 µl. In another embodiment, the reactor has a volume in the range of 1-1,000 ml, preferably 10-1,000 ml, more preferably 10-100 ml. In another embodiment, the reactor has a volume in the range of 1-10,000 L, preferably 100-1,000 L, more preferably 500-1,000 L. In a preferred embodiment, reaction conditions and the characteristics of the hydrogen gas and the alkyl-aromatic hydrocarbon stream are selected such that the $C_{9+}$ alkyl-aromatic hydrocarbon compounds present in the alkyl-aromatic hydrocarbon stream are converted to xylene. The catalytic reactions may include dealkylation, transalkylation, and/or disproportionation of the $C_{9+}$ alkyl-aromatic hydrocarbon compounds. Dealkylation refers to a chemical reaction whereby one or more alkyl groups (e.g. methyl, ethyl, propyl, butyl, etc.) are removed from a hydrocarbon compound. Dealkylation generally takes place in the presence of hydrogen gas and a catalyst. For example, dealkylation of methylethylbenzene may form toluene. Transalkylation, however, refers to a chemical reaction through which one or more alkyl groups (e.g. methyl, ethyl, propyl, butyl, etc.) are transferred from one organic compound to another. For example, transalkylation of a mixture containing toluene and trimethylbenzene may lead to the formation of xylene. Furthermore, disproportionation refers to a redox reaction in which an organic molecule is reduced in a reduction reaction, and the similar organic molecule is also oxidized in an oxidation reaction, thereby forming two different products. For example, disproportionation of toluene may form benzene (via an oxidation reaction), and xylene (via a reduction reaction).

In a preferred embodiment, the process further involves treating the zeolite catalyst with the hydrogen gas prior to the contacting. Treating the zeolite catalyst refers to a process whereby the zeolite catalyst is first oxidized and then reduced prior to the catalytic reactions. Accordingly, a temperature of the zeolite catalyst is raised to a temperature in the range of 450-550° C., preferably 450-500° C., more preferably about 450° C. from room temperature (i.e. about 25° C.) at a ramp rate of 2-10°/min, preferably 3-5° C./min, wherein the zeolite catalyst is treated with an air stream having a flow rate in the range of 10-50 ml/min, preferably 15-40 ml/min, more preferably 15-25 ml/min at an atmospheric pressure. The zeolite catalyst may be held isothermally at a temperature in the range of 450-550° C., preferably 450-500° C., more preferably about 450° C. for at least 6 hours, preferably at least 8 hours, more preferably at least 10 hours. After that, the temperature of the zeolite catalyst is equilibrated at a temperature in the range of 200-300° C., preferably 220-280° C., more preferably 250° C., while concurrently a hydrogen gas stream having a flow rate in the range of 10-50 ml/min, preferably 15-40 ml/min, more preferably 15-25 ml/min at an atmospheric pressure is contacted with the zeolite catalyst (for example by passing the hydrogen gas stream through a catalyst bed of the zeolite catalyst) for at least 2 hours, preferably at least 3 hours, more preferably at least 5 hours. Finally, the temperature of the zeolite catalyst is raised to a temperature in the range of 250-400° C., preferably 300-400° C., more preferably about 350° C. at a ramp rate of 2-10° C./min, preferably 3-5° C./min, while concurrently treating the zeolite catalyst with the hydrogen gas stream at an atmospheric pressure for at least 2 hours, preferably at least 3 hours, more preferably at least 5 hours.

Once the zeolite catalyst is reduced in the hydrogen gas, the alkyl-aromatic hydrocarbon stream may be contacted with the zeolite catalyst (for example by passing the alkyl-aromatic hydrocarbon stream through a catalyst bed of the zeolite catalyst) in the presence of the hydrogen gas. In one embodiment, the alkyl-aromatic hydrocarbon stream is delivered to a reactor having a catalyst volume of less than 100 ml, preferably less than 50 ml, more preferably less than 10 ml, wherein the alkyl-aromatic hydrocarbon stream has a flow rate in the range of 1-500 ml/h, preferably 10-400 ml/h, more preferably 20-250 ml/h during the contacting. In one embodiment, the alkyl-aromatic hydrocarbon stream is delivered to a reactor having a catalyst volume of at least 1 L, preferably at least 5 L, more preferably at least 10 L, but no more than 50 L, wherein the alkyl-aromatic hydrocarbon stream has a flow rate in the range of 1-250 L/h, preferably 2-200 L/h, more preferably 3-150 L/h during the contacting. In one embodiment, the alkyl-aromatic hydrocarbon stream is delivered to a reactor having a catalyst volume of at least 100 L, preferably at least 500 L, more preferably at least 1,000 L, but no more than 10,000 L, wherein the alkyl-aromatic hydrocarbon stream has a flow rate in the range of 1-50,000 L/h, preferably 100-40,000 L/h, more preferably 200-30,000 L/h during the contacting. In another embodiment, the alkyl-aromatic hydrocarbon stream has a liquid hourly space velocity in the range of 1-5 $h^{-1}$, preferably 1-4 $h^{-1}$, more preferably 1-3 $h^{-1}$, even more preferably about 2 $h^{-1}$ during the contacting.

In one embodiment, the reactor is a vertically oriented cylindrical vessel, wherein the alkyl-aromatic hydrocarbon stream enters the reactor from a top end or from a bottom end.

Hydrogen gas may also be introduced into the reactor having a catalyst volume of less than 100 ml, preferably less than 50 ml, more preferably less than 10 ml, with a flow rate in the range of 100-4,000 ml/min, preferably 200-3,000 ml/min, or more preferably 250-2,500 ml/min. Hydrogen gas may be introduced into the reactor having a catalyst volume of at least 1 L, preferably at least 5 L, more preferably at least 10 L, but no more than 50 L, with a flow rate in the range of 1-125,000 L/h, preferably 500-100,000 L/h, more preferably 1,000-60,000 L/h. Furthermore, hydrogen gas may be introduced into the reactor having a catalyst volume of at least 100 L, preferably at least 500 L, more preferably at least 1,000 L, but no more than 10,000 L, with a flow rate in the range of 25,000-2,500,000 L/h, preferably 50,000-2,000,000 L/h, more preferably 100,000-1,500,000 L/h. In a preferred embodiment, a molar ratio of the hydrogen gas to hydrocarbon compounds in the alkyl-aromatic hydrocarbon stream is in the range of 1:1-6:1, preferably 1:1-5:1, more preferably 1:1-4:1.

The hydrogen gas increases an internal pressure of the reactor to at least 1 MPa, or preferably at least 2 MPa, but no more than 3 MPa. In one embodiment, the hydrogen gas and the alkyl-aromatic hydrocarbon stream have a flow direction that is co-current one to another. In another embodiment, the hydrogen gas and the alkyl-aromatic hydrocarbon stream have a flow direction that is counter-current one to another.

The zeolite catalyst may be kept at an isothermal temperature range of 150-600° C., preferably 200-600° C., more preferably 200-500° C., even more preferably 300-400° C. during the catalytic reactions.

In one embodiment, the alkyl-aromatic hydrocarbon stream comprises toluene, methylethylbenzene, trimethylbenzene, dimethylethylbenzene, and tetramethylbenzene, and reaction conditions are selected such that each of the $C_{9+}$ alkyl-aromatic hydrocarbon compounds present in the alkyl-aromatic hydrocarbon stream are converted to xylene. Accordingly, a transalkylation reaction of trimethylbenzene and toluene to form xylenes is desirable. In one embodiment, methylethylbenzene is first dealkylated to form toluene, and the toluene is further converted to xylene via the transalkylation reaction with trimethylbenzene. Xylene may also be formed via disproportionation of toluene. Furthermore, xylene may be formed via transalkylation of toluene and methylethylbenzene. In one embodiment, production of xylene via the catalytic reactions that also produce heavy alkyl-aromatic compounds (i.e. $C_{10+}$) is not preferable. For example, disproportionation of trimethylbenzene is not desirable, as it also produces tetramethylbenzenes. The heavy alkyl-aromatic compounds (i.e. $C_{10+}$) may act as coke precursors and thus may poison/deactivate the zeolite catalyst. In one embodiment, the catalytic reactions that produce light hydrocarbons compounds (i.e. $C_{5-}$) are not preferable. In another embodiment, the catalytic reactions that produce hydrocarbon compounds having a boiling point difference of less than 10° C., preferably less than 5° C. to the boiling point of xylene is not preferable. For example, if a first catalytic reaction produces a hydrocarbon compound that has a boiling point which is 20° C. higher/lower than the boiling point of xylene (i.e. 138° C.), then the first catalytic reaction is desired, however, if a second catalytic reaction produces a hydrocarbon compound that has a boiling point which is less than 10° C. (e.g. 8° C.) higher/lower than the boiling point of xylene (i.e. 138° C.), then the second catalytic reaction is not desired. For example transalkylation of toluene and methylethylbenzene toward formation of xylene and ethylbenzene, or disproportionation of methylethylbenzene toward formation of ethylbenzene and dimethylethylbenzene is not desired, as each produces ethylbenzene that has a boiling point (i.e. 136° C.) of less than 10° C. to that of the xylene (i.e. 138° C.).

In a preferred embodiment, the alkyl-aromatic hydrocarbon stream comprises toluene, methylethylbenzene, trimethylbenzene, dimethylethylbenzene, and tetramethylbenzene, and the process further comprises reducing a toluene content of the alkyl-aromatic hydrocarbon stream in a separation unit prior to the contacting. The separation unit may preferably be a fractional distillation column, wherein the toluene content of the alkyl-aromatic hydrocarbon stream is reduced by heating the alkyl-aromatic hydrocarbon stream to the boiling point of toluene (i.e. about 110° C.) to form toluene vapors, and optionally condensing the toluene vapors in the fractional distillation column.

In one embodiment, the alkyl-aromatic hydrocarbon stream has an average methyl-to-benzene molar ratio (M/R) in the range of 2-3, preferably 2-2.8, more preferably 2-2.5 prior to the contacting. The average methyl-to-benzene molar ratio is a ratio of number/mole of methyl groups to number/mole of benzene rings in all hydrocarbon compounds present in a stream. If one stream contains x-mole of component α having a methyl-to-benzene molar ratio of A, y-mole of component β having a methyl-to-benzene molar ratio of B, and z-mole of component γ having a methyl-to-benzene molar ratio of C, the average methyl-to-benzene molar ratio of this stream can be calculated from the equation below:

$$\overline{M/R} = \frac{[xA + yB + zC]}{x + y + z}$$

For example, if the alkyl-aromatic hydrocarbon stream contains 3 moles of trimethylbenzene (with a methyl-to-benzene molar ratio of 3) and 3 moles of toluene (with a methyl-to-benzene molar ratio of 1), the average methyl-to-benzene molar ratio in this stream is $[(3\times3)\pm(3\times1)]/(3+3)=2$.

In one embodiment, toluene acts as an inhibitor in the transalkylation of trimethylbenzene and in dealkylation of methylethylbenzene toward producing xylene. Therefore, reducing the toluene content of the alkyl-aromatic hydrocarbon stream may increase a yield of xylene.

The process for converting the alkyl-aromatic hydrocarbon stream to the BTX-rich stream further involves separating $C_{5-}$ and $C_{9+}$ hydrocarbon compounds from a product stream to form the BTX-rich stream.

The product stream refers to an effluent of the reactor. In one embodiment, the product stream comprises, $C_1$-$C_4$ alkanes (e.g. methane, ethane, propane, and butane), benzene, toluene, xylene, methylethylbenzene, trimethylbenzene, and heavy alkyl-aromatic compounds (i.e. $C_{10+}$ such as dimethylethylbenzene and tetramethylbenzene). In one embodiment, a $C_1$-$C_4$ alkane content of the product stream is less than 10 wt %, preferably less than 5 wt %, more preferably less than 1 wt %. In another embodiment, a heavy alkyl-aromatic content of the product stream is less than 15 wt %, preferably less than 10 wt %, more preferably less than 5 wt %. In a preferred embodiment, a xylene content of the product stream is in the range of 10-50%, preferably 20-40%, more preferably 25-40% by weight. In another preferred embodiment, a content of benzene, toluene, and xylene in the product stream is at least 40 wt %, preferably at least 50 wt %, more preferably at least 60 wt %, even more preferably at least 70 wt %. Xylene in the product stream may be present in the form of meta-xylene, ortho-xylene, and/or para-xylene. The three isomers of xylene namely, meta-xylene, ortho-xylene and para-xylene were formed under the reaction conditions with a molar ratio of 2:1:1, preferably a molar ratio of 2.5:1:1, more preferably a molar ratio of 53:23:24, respectively.

In one embodiment, the yield of xylene as described by the process is in the range of 10-50%, preferably 20-40%, more preferably 25-40%, with the yield of xylene being a ratio of an amount of xylene (in weight) in the product stream to an amount (in weight) of the alkyl-aromatic hydrocarbon stream that is contacted with the zeolite catalyst. In addition, the process forms xylene with a selectivity in the range of 30-70%, preferably 40-60%, more preferably 50-60%, with selectivity being calculated by multiplying the yield of xylene by a degree of conversion of $C_9$ aromatics present in the alkyl-aromatic hydrocarbon stream.

In one embodiment, the $C_1$-$C_4$ alkanes present in the product stream is stripped in a stripping column to form a stripped product stream having a $C_1$-$C_4$ alkane content of less than 5 wt %, preferably less than 1 wt %, more preferably less than 0.5 wt %. Stripping refers to a process whereby one or more components of a liquid stream are removed by a vapor stream. Accordingly, a stripping column is a vessel, wherein a liquid phase is in direct contact with a vapor phase at a condition favorable for one or more components of the liquid phase to transfer to the vapor phase via a mass transport phenomenon. Exemplary stripping columns used herein may include, but are not limited to tray towers, packed columns, spray towers, and bubble columns.

In another embodiment, the heavy alkyl-aromatic compounds present in the product stream are also stripped to form the product stream having a heavy alkyl-aromatic content of less than 5 wt %, preferably less than 1 wt %, more preferably less than 0.5 wt %.

In a preferred embodiment, unreacted hydrocarbon compounds present in the product stream are also stripped to form the product stream having less than 5 wt %, preferably less than 1 wt %, more preferably less than 0.5 wt % of unreacted hydrocarbon compounds. The unreacted hydrocarbon compounds refer to the hydrocarbons present in the alkyl-aromatic hydrocarbon stream that are not converted to benzene, toluene, or xylene during the process. Examples of the unreacted hydrocarbon compounds mainly include, but are not limited to methylethylbenzene and trimethylbenzene.

The BTX-(benzene/toluene/xylene) rich stream comprises benzene, toluene, xylene, and one or more of $C_1$-$C_4$ alkanes (e.g. methane, ethane, propane, and butane), ethylbenzene, methylethylbenzene, diethylbenzene, trimethylbenzene, tetramethylbenzene, and dimethylethylbenzene, wherein the total weight of $C_1$-$C_4$ alkanes, ethylbenzene, methylethylbenzene, di ethylbenzene, trimethylbenzene, tetramethylbenzene, and dimethylethylbenzene is less than 30 wt %, preferably less than 20 wt %, more preferably less than 10 wt %, even more preferably less than 5 wt %. The total weight of benzene, toluene, and xylene (i.e. all isomers) in the BTX-rich stream is at least 70 wt %, preferably at least 80 wt %, more preferably at least 90 wt %, even more preferably at least 95 wt %, with weight percent being a ratio of a total weight of benzene, toluene, and xylene to the total weight of the BTX-rich stream. In one embodiment, a xylene content present in the BTX-rich stream is at least 40%, preferably at least 50%, more preferably at least 60% by weight.

The process for converting the alkyl-aromatic hydrocarbon stream to the BTX-rich stream may further involve separating xylene from the BTX-rich stream. In a preferred embodiment, the BTX-rich stream is delivered to a distillation unit to divide the BTX-rich stream into a benzene-rich stream, a toluene-rich stream, and a xylene-rich stream. A distillation unit as used herein refers to a unit whereby an aromatic raffinate influent (i.e. an aromatic-rich stream) is converted to the benzene-rich stream, the toluene-rich stream, and/or the xylene-rich stream based on a difference in boiling points of hydrocarbon compounds present in the aromatic raffinate influent. The distillation unit may comprise at least two, preferably at least three separation columns that are connected to each other in series, with the first column being a benzene column, the second column being a toluene column, and the third column being a xylene column. In one embodiment, at least a portion of the benzene present in the BTX-rich stream is separated in the benzene column. The benzene is further treated in a stripper and/or an absorber to form the benzene-rich stream, which may include at least 80%, preferably at least 90%, more preferably at least 95%, even more preferably at least 99% benzene by weight. A bottom effluent of the benzene column is delivered to the toluene column, wherein at least a portion of the toluene present in the BTX-rich stream is separated from the BTX-rich stream. The toluene may further be purified in a stripper and/or an absorber to form the toluene-rich stream, which may include at least 80%, preferably at least 90%, more preferably at least 95%, even more preferably at least 99% toluene by weight. A bottom effluent of the toluene column may further be treated in the xylene column, wherein the xylene-rich stream is produced, which may include at least 80%, preferably at least 90%, more preferably at least 95%, even more preferably at least 99% xylene by weight. The xylene-rich stream may have one or more of meta-xylene, ortho-xylene, and para-xylene, and the distillation unit may further include one or more separation columns, wherein meta-xylene, ortho-xylene, and para-xylene are separated from each other. A bottom effluent of the xylene column may first be dealkylated and further be recycled to the benzene column to increase a production yield of benzene, toluene, and/or xylene.

The zeolite catalyst includes a) a pillared MWW zeolite, and b) at least two metals selected from the group consisting of Pt, Re, Mo, and Ni.

Zeolites are alumino-silicate minerals that occur in nature. Elementary building units of zeolites are $SiO_4$ and $AlO_4$ tetrahedra. Adjacent tetrahedra are linked at their corners via a common oxygen atom, which results in an inorganic macromolecule with a three-dimensional framework. The three-dimensional framework of a zeolite also comprises channels, channel intersections, and/or cages having dimensions in the range of 0.1-10 nm, preferably 0.2-5 nm, more preferably 0.2-2 nm. Water molecules may be present inside these channels, channel intersections, and/or cages.

MWW zeolite refers to a type of zeolite that comprises at least two independent sets of 10-membered ring channels. In one embodiment, aluminum containing MWW zeolite (i.e. MCM-22) is used, wherein a silicon-to-aluminum molar ratio in the zeolite catalyst is at least 40, or preferably at least 45, or preferably at least 50, but no more than 100. In another embodiment, the MWW zeolite catalyst comprises micro-pores (i.e. pores having an average pore diameter of less than 2 nm) having a specific pore volume in the range of 0.1-0.3 $cm^3$/g, preferably 0.1-0.2 $cm^3$/g, more preferably 0.15-0.2 $cm^3$/g, and meso-pores (i.e. pores having an average pore diameters in the range of 2-50 nm) having a specific pore volume in the range of 0.01-0.15 $cm^3$/g, preferably 0.05-0.15 $cm^3$/g, more preferably 0.05-0.1 $cm^3$/g. In one embodiment, a specific pore volume of macro-pores (i.e. pores having an average pore diameter of above 50 nm) in the pillared MWW zeolite is less than 0.2 $cm^3$/g, preferably less than 0.1 cm$^3$/g, more preferably less than 0.01 cm$^3$/g. In one embodiment, a specific surface area of the micro-pores in the pillared MWW zeolite is in the range of 100-500 m$^2$/g, preferably 300-500 m$^2$/g, more preferably about 400 m$^2$/g, whereas a specific surface area of the meso-pores in the pillared MWW zeolite is in the range of 50-150 m$^2$/g, preferably 50-100 m$^2$/g, more preferably about 80 m$^2$/g. A specific surface area of the macro-pores in the pillared MWW zeolite may be in the range of 500-1,000 m$^2$/g, preferably 700-1,000 m$^2$/g, more preferably about 850 m$^2$/g. In another embodiment, an average pore diameter of the micro-pores, the meso-pores, and the macro-pores in the pillared MWW zeolite is in the range of 1-10 nm, preferably 2-6 nm, more preferably about 5 nm. In one embodiment, a total acidity of the pillared MWW zeolite is in the range of 2-10 mmol/g, preferably 5-10 mmol/g, more preferably about 7.5 mmol/g. The MWW zeolite may be in the form of pellets having a diameter in the range of 0.5-5 mm, preferably 0.5-1.5 mm, more preferably about 1 mm. The MWW zeolite catalyst may also be extrudated to have a geometry selected from the group consisting of cylindrical, rectilinear, star-shaped, conical, pyramidal, rectangular, cubical, and ring-shaped.

The zeolite catalyst may be one or more selected from the group consisting of a 4-membered ring zeolite, a 6-membered ring zeolite, a 10-membered ring zeolite, and a 12-membered ring zeolite. The zeolite catalyst may have a zeolite with a natrolite framework (e.g. gonnardite, natrolite, mesolite, paranatrolite, scolecite, and tetranatrolite), edingtonite framework (e.g. edingtonite and kalborsite), thomsonite framework, analcime framework (e.g. analcime, leucite, pollucite, and wairakite), phillipsite framework (e.g. harmotome), gismondine framework (e.g. amicite, gismondine, garronite, and gobbinsite), chabazite framework (e.g. chabazite-series, herschelite, willhendersonite, and SSZ-13), faujasite framework (e.g. faujasite-series, Linde type X, and Linde type Y), mordenite framework (e.g. maricopaite and mordenite), heulandite framework (e.g. clinoptilolite and heulandite-series), stilbite framework (e.g. barrerite, stellerite, and stilbite-series), brewsterite framework, or cowlesite/ZSM-5 framework.

The pillared MWW zeolite is a type of zeolite, wherein pillars are located between two adjacent layers in the MWW zeolite. In one embodiment, the pillared MWW zeolite comprises silica pillars. In a preferred embodiment, the pillared MWW zeolite is a 12-membered ring zeolite catalyst. In one embodiment, the pillared MWW zeolite comprises micro-pores (i.e. pores having an average pore diameter of less than 2 nm) having a specific pore volume in the range of 0.01-0.2 cm$^3$/g, preferably 0.05-0.2 cm$^3$/g, more preferably 0.05-0.1 cm$^3$/g, and meso-pores (i.e. pores having an average pore diameters in the range of 2-50 nm) having a specific pore volume in the range of 0.1-0.5 cm$^3$/g, preferably 0.2-0.5 cm$^3$/g, more preferably 0.3-0.5 cm$^3$/g. In one embodiment, a specific pore volume of macro-pores (i.e. pores having an average pore diameter of above 50 nm) in the pillared MWW zeolite is less than 0.2 cm$^3$/g, preferably less than 0.1 cm$^3$/g, more preferably less than 0.01 cm$^3$/g. In one embodiment, a specific surface area of the micro-pores in the pillared MWW zeolite is in the range of 100-200 m$^2$/g, preferably 150-200 m$^2$/g, more preferably about 175 m$^2$/g, whereas a specific surface area of the meso-pores in the pillared MWW zeolite is in the range of 400-500 m$^2$/g, preferably 400-450 m$^2$/g, more preferably about 430 m$^2$/g. A specific surface area of the macro-pores in the pillared MWW zeolite may be in the range of 500-1,000 m$^2$/g, preferably 700-1,000 m$^2$/g, and more preferably about 850 m$^2$/g. In another embodiment, an average pore diameter of the micro-pores, the meso-pores, and the macro-pores in the pillared MWW zeolite is in the range of 1-10 nm, preferably 2-6 nm, more preferably about 4 nm. In one embodiment, a total acidity of the pillared MWW zeolite is in the range of 2-10 mmol/g, preferably 4-8 mmol/g, and more preferably about 6.2 mmol/g. The method of producing the pillared MWW zeolite is discussed in the third aspect of this disclosure.

In one embodiment, the at least two metals in the zeolite catalyst are transition metals selected from groups 6-10 of the periodic table. In a preferred embodiment, the zeolite catalyst comprises platinum (Pt) which is present in the catalyst in an amount in the range of 0.1-1 wt %, preferably 0.1-0.8 wt %, more preferably 0.1-0.6 wt %, even more preferably 0.1-0.4 wt %, with weight percent being relative to the total weight of the zeolite catalyst. In another preferred embodiment, the zeolite catalyst comprises Pt having a composition in the range of 0.1-1 wt %, preferably 0.1-0.8 wt %, more preferably 0.1-0.6 wt %, even more preferably 0.1-0.4 wt %, and rhenium (Re) having a composition in the range of 0.1-1 wt %, preferably 0.1-0.3 wt %, more preferably about 0.1-0.2 wt %, with weight percent being relative to the total weight of the zeolite catalyst. In the most preferred embodiment, the zeolite catalyst comprises 0.4 wt % Pt and 0.2 wt % Re. In a preferred embodiment, the transition metals are evenly dispersed within the zeolite catalyst. The MWW zeolite catalyst includes intra-crystalline and inter-crystalline pores, and the transition metals may be located at the inter-crystalline pores or preferably at the intra-crystalline pores.

According to a second aspect of the present disclosure relates to a process for converting an alkyl-aromatic hydrocarbon stream to a BTX-rich stream, involving contacting the alkyl-aromatic hydrocarbon stream with a zeolite catalyst in the presence of the hydrogen gas. The hydrogen gas may be at a temperature in the range of 150-600° C., preferably 200-600° C., more preferably 200-500° C., even more preferably 300-400° C. and a pressure of at least 1 MPa, or preferably at least 2 MPa, but no more than 3 MPa to form a product stream.

A molar ratio of the hydrogen gas to hydrocarbon compounds in the alkyl-aromatic hydrocarbon stream is in the range of 1:1-6:1, preferably 1:1-5:1, more preferably 1:1-4:1. The alkyl-aromatic hydrocarbon stream has a space velocity in the range of 1-5 h$^{-1}$, preferably 1-4 h$^{-1}$, more preferably 1-3 h$^{-1}$, even more preferably about 2 h$^{-1}$.

The process for converting an alkyl-aromatic hydrocarbon stream to a BTX-rich stream according to the second aspect further involves separating C$_{5-}$ and C$_{9+}$ hydrocarbon compounds from the product stream to form the BTX-rich stream.

Processing steps of the second aspect have been described previously in the first aspect of the present disclosure.

The zeolite catalyst includes a) a delaminated MWW zeolite, and b) at least two metals selected from the group consisting of Pt, Re, Mo, and Ni.

In one embodiment, the zeolite catalyst includes micro-pores having a specific pore volume in the range of 0.03-0.07 cm$^3$/g, and meso-pores having a specific pore volume in the range of 0.7-0.75 cm$^3$/g.

In one embodiment, the yield of xylene as described by the process of the second aspect is in the range of 10-30%, preferably 10-25%, more preferably 15-20%, with the yield of xylene being a ratio of an amount of xylene (in weight) in the product stream to an amount (in weight) of the alkyl-aromatic hydrocarbon stream that is contacted with the zeolite catalyst. In addition, the process of the second aspect forms xylene with a selectivity in the range of 30-50%, preferably 35-45%, more preferably about 40%, with selectivity being calculated by multiplying the yield of xylene by a degree of conversion of $C_9$ aromatics present in the alkyl-aromatic hydrocarbon stream.

In one embodiment, the delaminated MWW zeolite comprises micro-pores (i.e. pores having an average pore diameter of less than 2 nm) having a specific pore volume in the range of 0.01-0.2 cm$^3$/g, preferably 0.01-0.1 cm$^3$/g, more preferably 0.01-0.06 cm$^3$/g, and meso-pores (i.e. pores having an average pore diameters in the range of 2-50 nm) having a specific pore volume in the range of 0.3-0.8 cm$^3$/g, preferably 0.5-0.8 cm$^3$/g, more preferably 0.7-0.8 cm$^3$/g. In one embodiment, a specific pore volume of macro-pores (i.e. pores having an average pore diameter of above 50 nm) in the delaminated MWW zeolite is less than 0.2 cm$^3$/g, preferably less than 0.1 cm$^3$/g, more preferably less than 0.01 cm$^3$/g. In one embodiment, a specific surface area of the micro-pores in the delaminated MWW zeolite is in the range of 50-150 m$^2$/g, preferably 100-150 m$^2$/g, more preferably about 120 m$^2$/g, whereas a specific surface area of the meso-pores in the delaminated MWW zeolite is in the range of 500-800 m$^2$/g, preferably 600-700 m$^2$/g, more preferably about 650 m$^2$/g. A specific surface area of the macro-pores in the delaminated MWW zeolite may be in the range of 500-1,000 m$^2$/g, preferably 700-1,000 m$^2$/g, more preferably about 850 m$^2$/g. In another embodiment, an average pore diameter of the micro-pores, the meso-pores, and the macro-pores in the delaminated MWW zeolite is in the range of 1-10 nm, preferably 5-10 nm, more preferably about 8 nm. In one embodiment, a total acidity of the delaminated MWW zeolite is in the range of 2-10 mmol/g, preferably 4-8 mmol/g, more preferably about 7 mmol/g. The method of producing the delaminated MWW zeolite is discussed in the third aspect of this disclosure. The delaminated MWW zeolite catalyst may also be extrudated to have a geometry selected from the group consisting of cylindrical, rectilinear, star-shaped, conical, pyramidal, rectangular, cubical, and ring-shaped.

The MWW zeolite has a layered structure, therefore, the delaminated MWW zeolite refers to a structural topology, wherein layers in the MWW zeolite are exfoliated and are only adjacent to each other with no regular pattern. In contrast, the pillared MWW zeolite refers to a structural topology, wherein layers in the MWW zeolite are exfoliated and located parallel one to another having pillars therebetween. Both of the delaminated MWW zeolite and the pillared MWW zeolite have higher specific volumes compare to that of the MWW zeolite. A specific volume of the delaminated MWW zeolite may be higher than a specific volume of the pillared MWW zeolite.

In one embodiment, the at least two metals in the zeolite catalyst are transition metals selected from groups 6-10 of the periodic table. In a preferred embodiment, the zeolite catalyst comprises platinum (Pt) having a composition in the range of 0.1-1 wt %, preferably 0.1-0.8 wt %, more preferably 0.1-0.6 wt %, even more preferably 0.1-0.4 wt %, with weight percent being relative to the total weight of the zeolite catalyst. In another preferred embodiment, the zeolite catalyst comprises Pt having a composition in the range of 0.1-1 wt %, preferably 0.1-0.8 wt %, more preferably 0.1-0.6 wt %, even more preferably 0.1-0.4 wt %, and rhenium (Re) having a composition in the range of 0.1-1 wt %, preferably 0.1-0.3 wt %, more preferably about 0.1-0.2 wt %, with weight percent being relative to the total weight of the zeolite catalyst.

According to a third aspect the present disclosure relates to a method of preparing a metal-doped pillared zeolite catalyst. The method involves treating a MWW zeolite (e.g. MCM-22) with an ammonium halide solution at a temperature in the range of 50-120° C., preferably 50-100° C., more preferably 80° C. for at least 18 hours, preferably at least 20 hours, more preferably at least 24 hours to form an intercalated MCM-22 zeolite. Exemplary ammonium halide solutions may include, but are not limited to ammonium chloride, ammonium bromide, ammonium iodide, cetyltrimethylammonium chloride, cetyltrimethylammonium bromide, cetyltrimethylammonium iodide, cetyltriethylammonium bromide, cetyltriethylammonium chloride, cetyltriethylammonium iodide, tetrapropylammonium hydroxide, tetraethylammonium hydroxide, tetramethylammonium hydroxide, or any combination thereof.

In one embodiment, a pH level of the intercalated MCM-22 zeolite is reduced to less than 2, preferably less than 1.5 by adding a hydrohalic acid (e.g. hydrochloric acid), and the intercalated MCM-22 zeolite is optionally centrifuged at a rotational speed of at least 20,000 rpm, preferably at least 22,000, more preferably at least 25,000 rpm.

The method further involves treating the intercalated MCM-22 zeolite with a silicate solution at a temperature in the range of 50-120° C., preferably 50-100° C., more preferably 80° C. and at an inert environment for at least 20 hours, preferably at least 22 hours, more preferably at least 25 hours to form a pillared MCM-22 zeolite. In one embodiment, a weight ratio of the intercalated MCM-22 zeolite to the silicate solution is in the range of 0.1-0.5 wt/wt, preferably 0.1-0.3 wt/wt, more preferably about 0.2 wt/wt.

Exemplary silicate solutions may include, but are not limited to sodium silicate, tetramethylammonium silicate, sodium metasilicate, and tetraethylortho silicate. The inert environment may refer to an environment, wherein concentration of oxygen is less than 100 ppm, preferably less than 50 ppm, more preferably less than 10 ppm. The inert environment may be a nitrogen-filled, environment, an argon-filled environment, or a combination thereof.

The method further involves treating the pillared MCM-22 zeolite with an ammonium nitrate solution in an inert environment at a temperature in the range of 50-120° C., preferably 50-100° C., more preferably 80° C. for at least 6 hours, preferably at least 8 hours, more preferably at least 10 hours, followed by calcining the pillared MCM-22 zeolite in an oxygen containing atmosphere at a temperature in the range of 200-600° C., or preferably 400-600° C., more preferably 500-600° C. to form a (X,H)MCM-36 zeolite, wherein X is an alkali metal, preferably Na. The ammonium nitrate solution may have a molar concentration in the range of 1-3 M, preferably 1.5-2.5 M, more preferably about 2 M. The oxygen containing atmosphere may refer to an environment having an oxygen content of at least 20 vol %, preferably at least 50 vol %, more preferably at least 90 vol %. Exemplary oxygen containing atmospheres include air or pure oxygen atmosphere.

The method further involves treating the (X,H)MCM-36 zeolite with the ammonium halide solution at a temperature in the range of 50-120° C., preferably 50-100° C., more preferably 80° C. for at least 6 hours, preferably at least 8 hours, more preferably at least 10 hours, followed by calcining the pillared MCM-22 zeolite in the oxygen containing atmosphere at a temperature in the range of 200-600° C., or preferably 400-600° C., more preferably 500-600° C. to form a H-MCM-36 zeolite.

The method further involves treating the H-MCM-36 zeolite with a platinum solution at a temperature in the range of 50-120° C., preferably 50-100° C., more preferably 80° C. for at least 12 hours, preferably at least 13 hours, more preferably at least 15 hours to form a Pt-MCM-36 zeolite, wherein a composition of Pt is in the range of 0.1-1 wt %, preferably 0.1-0.8 wt %, more preferably 0.1-0.6 wt %, even more preferably 0.1-0.4 wt %, with weight percent being relative to the total weight of the zeolite catalyst. Exemplary platinum solutions may include various platinum sources including, but not limited to chloroplatinic acid (i.e. $H_2(PtCl_6) \cdot H_2O$), tetraammineplatinum(II) nitrate (i.e. $Pt(NH_3)_4(NO_3)_2$), platinum(0)-2,4,6,8-tetramethyl-2,4,6,8-tetravinylcyclotetrasiloxane, platinum(0)-1,3-divinyl-1, 1,3, 3-tetramethyldisiloxane, or any combination thereof.

In one embodiment, the method further involves oxidizing the Pt-MCM-36 zeolite in an oxygen containing atmosphere. Accordingly, the Pt-MCM-36 zeolite is first maintained isothermally at a temperature in the range of 100-200° C., preferably 130-150° C., more preferably about 140° C., for 1 hour, preferably 2 hours. Further, the Pt-MCM-36 zeolite is maintained isothermally at a temperature in the range of 300-400° C., preferably 330-370° C., more preferably about 350° C. for 1 hour, preferably 2 hours. Finally, the Pt-MCM-36 zeolite is maintained isothermally at a temperature in the range of 400-500° C., preferably 440-460° C., more preferably about 450° C. for 5 hours, preferably 6 hours. In one embodiment, the Pt-MCM-36 zeolite is dried under a nitrogen flow with a flow rate in the range of 10-50 ml/min, preferably 15-40 ml/min, more preferably 15-25 ml/min, and at a temperature in the range of 300-400° C., preferably 330-370° C., more preferably about 350° C. for 2 hours, preferably 3 hours. In one embodiment, the Pt-MCM-36 zeolite is reduced with a hydrogen gas with a flow rate in the range of 10-50 ml/min, preferably 15-40 ml/min, more preferably 15-25 ml/min.

In a preferred embodiment, the method further involves treating the Pt-MCM-36 zeolite with a rhenium solution (e.g. ammonium perrhenate ($NH_4ReO_4$)), followed by calcining in the oxygen containing atmosphere at a temperature in the range of 200-600° C., or preferably 400-600° C., more preferably 500-600° C. to form a Re/Pt-MCM-36 zeolite, wherein a composition of Re is in the range of 0.1-1 wt %, preferably 0.1-0.3 wt %, more preferably about 0.1-0.2 wt %, with weight percent being relative to the total weight of the zeolite catalyst. In one embodiment, the method further involves drying the Pt-MCM-36 zeolite in an inert atmosphere in a temperature range of 200-600° C., preferably 300-400° C. prior to reducing the Pt-MCM-36 zeolite with a hydrogen gas.

In one embodiment, a delaminated MWW zeolite is produced from the intercalated MCM-22 zeolite. Accordingly, the intercalated MCM-22 zeolite is first sonicated with a sonicater at a temperature in the range of 10-50° C., preferably 10-40° C., more preferably 20-30° C. for at least 20 mins, preferably at least 30 mins, more preferably at least 40 mins. A pH level of the intercalated MCM-22 zeolite is then reduced to less than 2, preferably less than 1.5 by adding a hydrohalic acid (e.g. hydrochloric acid), while the intercalated MCM-22 zeolite is centrifuged at a rotational speed of at least 20,000 rpm, preferably at least 22,000, more preferably at least 25,000 rpm. Centrifuged intercalated MCM-22 zeolite is washed with water and calcined at a temperature in the range of 200-600° C., or preferably 400-600° C., more preferably 500-600° C. Calcined intercalated MCM-22 zeolite is finally treated with the ammonium halide solution at a temperature in the range of 50-120° C., preferably 50-100° C., more preferably 80° C. for at least 8 hours, preferably at least 10 hours, more preferably at least 12 hours, followed by calcining at a temperature in the range of 200-600° C., or preferably 400-600° C., more preferably 500-600° C. for at least 8 hours, preferably at least 10 hours, more preferably at least 12 hours to form a delaminated MCM-22 zeolite.

The examples below are intended to further illustrate protocols for the process of converting alkyl-aromatic hydrocarbons to BTX (benzene/toluene/xylene), and also methods of preparing metal-doped pillared/delaminated zeolite catalysts, and are not intended to limit the scope of the claims.

EXAMPLE 1

Production of xylene from heavy aromatics is investigated. More specifically, yield of formation of xylene over metal modified zeolite catalysts is scrutinized. Due to the importance of zeolite topology in dealkylation-transalkylation reactions, it is preferable to utilize zeolites with tailorable pore structure. In this example, a two-dimensional layered MWW zeolite (MCM-22) was synthesized and its pore volume was increased by delamination and pillarization. Different amounts of Pt and Re were loaded over the zeolites and their performance for the dealkylation-transalkylation reactions was compared to mordenite.

EXAMPLE 2

H-Mordenite ($SiO_2/Al_2O_3=20$), denoted as H-MOR (acquired from PQ Corporation) was used without any after-treatment as a reference. Chloroplatinic acid solution [$H_2(PtCl_6) \cdot H_2O$] and tetraammineplatinum (II) nitrate [$Pt(NH_3)_4(NO_3)_2$] were used as sources of platinum, while ammonium perrhenate (VII) [$NH_4ReO_4$] as a source of rhenium. Analytical grade (99% purity) toluene, 1,2,4-trimethylbenzene (TMB), 1,3-methyl ethyl benzene (MEB) were used for preparing model feeds. These chemicals were obtained from Sigma-Aldrich and were used without any further purification.

Two model feeds were prepared using pure chemicals for performance evaluation of catalysts. The composition of these model feeds are as follows: (i) Feed A: TMB 65 wt. %+MEB 35 wt. %; and (ii) Feed B: TMB 60 wt. %+MEB 30 wt. %+toluene 10 wt. %. The composition of first feed was selected to simulate the real heavy reformate composition [S. Ali, M. Ali, K. Al-Nawad, C. Ercan, Y. Wang, Appl. Catal., A. 393 (1-2) 96-108], while composition of the second feed represents co-processing of heavy reformate and toluene.

EXAMPLE 3

A two-dimensional layered MWW zeolite (MCM-22) was synthesized and its pore volume was increased by delamination and pillarization to form ITQ-2 and MCM-36, respectively. The preparation methods are summarized below:

According to the procedure reported by Tsai et al. [T. C. Tsai, I. Wang J. Catal. 133 (1992) 136-145], MCM-22 was prepared from the mixture using hexamethylenimine (HMI) template with molar ratios of $SiO_2/Al_2O_3=50$; $OH^-/SiO_2=0.1$; $Na^+/SiO_2=0.2$; $HMI/SiO_2$ 0.35; $H_2O/SiO_2=25$. Briefly, Solution A was prepared from 29.4 g colloidal silica solution HS-40 and 9 g water. Solution B was prepared by mixing 0.5 g NaOH, 1.13 g $NaAlO_2$ and 27.3 g water. Solution B was then added with Solution A, 5.09 g HMI and at last 9 g water. The mixture was capped and stirred at 600 rpm for 10 minutes. Finally 0.16 g MCM-22 crystal counted as 0.2% of silica source was added to the mixture for seeded crystallization at the hydrothermal condition of 170° C. for 4 days under continuous stirring at 550 rpm. A solid product, denoted as M22-P (MCM-22 precursor), was received by filtration of the crystallization mixture, following with water washed and air drying at 60° C. for 6 h. (Na,H)M22 was obtained from M22-P by calcination in the oxygen containing atmosphere at 540° C. for 8 h. The H-M22 product denoted as M22 was prepared from (Na,H)M22 by ion-exchange for three times with NH$_4$Cl solution at 80° C. and 8 h, then drying and calcination in the oxygen containing atmosphere at 540° C. for 8 h.

The intercalated M22 sample, denoted as MWW-S, was prepared from M22-P by refluxing with the solution of cetyltrimethylammonium chloride (CTMAC) and tetrapropylammonium hydroxide (TPAOH) at 80° C. for 24 h. The MWW-S was subjected to a series of treatments for the preparation of (Na.H)ITQ2 sequentially with supersonication below 50° C. for 20 minutes, addition of 37% HCl solution till pH <2, centrifuge recovery at 20,000 rpm and water washing, drying and air calcination at 540° C. for 8 h. H-ITQ2 was prepared from (Na,H)ITQ2 by ion exchange for three times with NH$_4$Cl solution at 80° C. and 8 h, then drying and calcination in the oxygen containing atmosphere at 540° C. for 8 h.

The intercalated M22-S was recovered with centrifuge at 20,000 rpm, water washed, and dried. M22-S was pillared with tetra-ethyl-orthosilicate (TEOS) by refluxing the mixture of M22-S/TEOS at a ratio of 0.2 wt/wt at 80° C. under nitrogen for 25 h. The solid product per gram was mixed with 20 mL 2M NH$_4$NO$_3$ at 80° C. under nitrogen for 6 h for hydrolysis twice. The solid product was recovered and calcined in the oxygen containing atmosphere at 540° C. for 8 h to prepare (Na,H)M36. The H-MCM-36 product denoted as H-M36 was prepared from (Na,H)M36 by ion-exchange for three times with NH$_4$Cl solution at 80° C. and 8 h, then drying and calcination in the oxygen containing atmosphere at 540° C. for 8 h.

EXAMPLE 4

The H-MOR, H-M22, H-ITQ2, and H-MCM-36 zeolites were loaded with a single metal (Pt) or two metals (Pt and Re) to synthesize a series of catalysts having a range of pore size and metal type/content.

Metal containing zeolite catalysts were prepared from the H-zeolite by either ion exchange or incipient wetness impregnation procedure. The Pt/zeolite series, sample 1Pt/MOR, 2Pt/MOR and 4Pt/MOR representing Pt content of 0.1, 0.2 and 0.4 wt %, respectively, was prepared from H-MOR by incipient wetness impregnation with H$_2$(PtCl$_6$). H$_2$O solution. The 4Pt-zeolite series containing 0.4 wt % Pt, sample 4Pt-MOR, 4Pt-M22 and 4Pt-IQ2, were prepared from H-MOR, H-M22 and H-ITQ2, respectively, by ion exchange with Pt(NH$_3$)$_4$(NO$_3$)$_2$ aqueous solution at 80° C. for 12 h.

The bimetallic xRe/yPt-zeolite samples are denoted for a zeolite sample containing 0.y wt % Pt by ion exchange and 0.x wt % Re by impregnation. The bimetallic samples were prepared by introducing Re metal onto the oxidized Pt-zeolite samples by incipient wetness impregnation with an aqueous solution of NH$_4$ReO$_4$, followed by drying and calcination at 540° C. for 8 h.

The samples were oxidized in air with a heating protocol: a) heating to 140° C. and maintaining for 2 h, b) heating to 350° C. and maintaining for 2 h, c) heating to 450° C. and maintaining for 6 h, d) cooling down to room temperature. The oxidized samples were first dried under nitrogen flow at 350° C. for 2 h and then reduced under hydrogen gas at flow rate of 15-25 cc/min.

A list of the catalysts used in this study along with the sample ID, type of zeolite, metal(s) content, and metal incorporation procedure(s) is presented in Table 1.

TABLE 1

Description and composition of metal zeolites

| Type | Sample ID | Zeolite* | Metal(s) Content and its Incorporation Method(s) |
|---|---|---|---|
| Pt Zeolites | 1Pt/MOR | H- MOR (20) | 0.1 wt % Pt (Impregnation) |
|  | 2Pt/MOR | H- MOR (20) | 0.2 wt % Pt (Impregnation) |
|  | 4Pt/MOR | H- MOR (20) | 0.4 wt % Pt (Impregnation) |
|  | 4Pt-MOR | H- MOR (20) | 0.4 wt % Pt (Ion Exchange) |
|  | 4Pt-M22 | H-MCM-22 (50) | 0.4 wt % Pt (Ion Exchange) |
|  | 4Pt-IQ2 | H-ITQ-2 (50) | 0.4 wt % Pt (Ion Exchange) |
| Pt Re Zeolites | 2Re/4Pt-M22 | H-MCM-22 (50) | 0.4 wt % Pt (Ion Exchange) → oxidized → 0.2 wt % Re (Impregnation) → dried |
|  | 2Re/2Pt-M22 | H-MCM-22 (50) | 0.2 wt % Pt (Ion Exchange) → oxidized → 0.2 wt % Re (Impregnation) → dried |
|  | 2Re/4Pt-IQ2 | H-ITQ-2 (50) | 0.4 wt % Pt (Ion Exchange) → oxidized → 0.2 wt % Re (Impregnation) → dried |
|  | 2Re/2Pt-IQ2 | H-ITQ-2 (50) | 0.2 wt % Pt (Ion Exchange) → oxidized → 0.2 wt % Re (Impregnation) → dried |
|  | 2Re/4Pt-M36 | H-MCM-36 (50) | 0.4 wt % Pt (Ion Exchange) → oxidized → 0.2 wt % Re (Impregnation) → dried |

*The numbers in parenthesis indicate SiO$_2$/Al$_2$O$_3$ ratio

EXAMPLE 5

The framework structure of solid powder was measured with a Rigaku Multiflex X-ray Diffractometer using Cu$_{K\alpha}$ radiation.

Nitrogen adsorption-desorption isotherms and BET surface area measurements were conducted using Micromeritics ASAP2020 at 77 K. The samples of 0.1-0.15 g were first degassed in vacuum at a ramp rate of 10° C./min up to 350° C. for 8 h. The BET method was used to calculate the specific surface areas. The pore volumes and pore size distributions were derived from the desorption isotherms using the Barrett-Joyner-Halenda (BJH) method.

Ammonia TPD was recorded using a flow through micro reactor system connected to a gas chromatograph equipped with a thermal conductivity detector with a modified procedure reported by Lonyi and Valyon [F. Lonyi and J. Valyon, Micro. Mes. Mat., 47 (2001) 293-301]. Catalyst sample of 50 mg was pretreated at 350° C. in helium flowing gas for 1 h and then cooled down to 130° C. The sample was purged with $NH_3$ gas at 130° C. for 1 h and then evacuated at 250° C. to remove excess ammonia at the same temperature for 30 min. $NH_3$ desorption was conducted by heating the sample from 250° C. to 600° C. at a heating rate of 10° C./min.

Chemisorption of CO was carried out using Micromeritics ASAP2020. Before the measurements, the oxidized metal containing zeolite catalyst of 0.1 g was in-situ pre-dried under vacuum at 100° C. for 30 minutes, backfilled with helium and then reduced under $H_2$ at 400° C. for 1 h. CO Adsorption over the reduced metal catalyst was conducted at 35° C. and different pressures between 100 and 450 mmHg at 50 mmHg interval and 30 minutes of equilibration time. Metal dispersion was calculated from chemisorption volume by subtraction of physisorption volume from total sorption volume. The equipment was calibrated with a standard $Pt/Al_2O_3$ catalyst (0.5% Pt) determined as Pt dispersion of 35%.

EXAMPLE 6

Performance evaluation of the catalysts was conducted using a bench-top reactor system (Autoclave Engineers), which is an oven-based reactor system that keeps process fluid in a vaporized state. Catalyst (2 ml) was loaded in the fixed-bed micro-reactor as pellets (diameter=1 mm) without dilution. Inert alumina spheres (1 mm) were loaded at the top and the bottom of the catalyst bed. The catalyst samples were oxidized and then reduced in-situ as an activation procedure prior to catalytic reaction. The typical reduction procedure was as follows: (i) heating a catalyst sample at atmospheric pressure in $O_2/N_2$ flow at 15-25 cc/min by raising the reactor temperature from room temperature to 450° C. at ramp of 3-5° C./min and holding at 450° C. for 6 h, then reducing the reactor temperature down to 250° C.; (ii) switching to hydrogen gas at atmospheric pressure at flow rate of 15-25 cc/min at 250° C. and holding for 2 h; (iii) raising reactor temperature to 350° C. at ramp of 3-5° C./min at atmospheric pressure and holding for 2 h in hydrogen stream; (iv) adjusting the reactor system to a desirable reaction condition.

Model feeds containing alkylaromatics (Feed A or Feed B) and hydrogen were concurrently passed through the catalyst bed in a down-flow mode at a hydrogen pressure of 300 psi. The feed rate was 4.8 ml/h to maintain the liquid hourly space velocity (LHSV) at 2.4 $h^{-1}$. Hydrogen flow rate was kept at 50 ml/min at the inlet of the reactor. The performance of catalysts was investigated at 350 and 400° C.

The reactor system was equipped with a gas-liquid separation system with continuous operation. Starting with lowest severity, each set of process conditions was maintained for at least 3 h to ensure steady-state. Liquid and gaseous product samples were collected separately after three hours of steady state operation at constant process conditions.

Feeds and reaction products were analyzed by an Agilent 6890N Gas Chromatograph equipped with a flame ionization detector (FID) and a capillary column INNOWAX, 60-m cross-linked polyethylene glycol with an internal diameter of 0.32 mm.

EXAMPLE 7

X-ray diffraction patterns of H-MCM-22, MWW-S, H-ITQ-2, and H-MCM-36 are shown in FIG. 1. The XRD diffractogram confirmed a typical pattern of MCM-22 framework structure exhibiting a main peak at the diffraction angle of 2θ=25.9 degrees. The XRD diffractogram of MWW-S exhibited a low angle diffraction peak, which indicated an intercalation of CTMAC. The XRD diffractograms of ITQ-2 and MCM-36 confirmed pure MWW zeolite structure.

Figure 2:
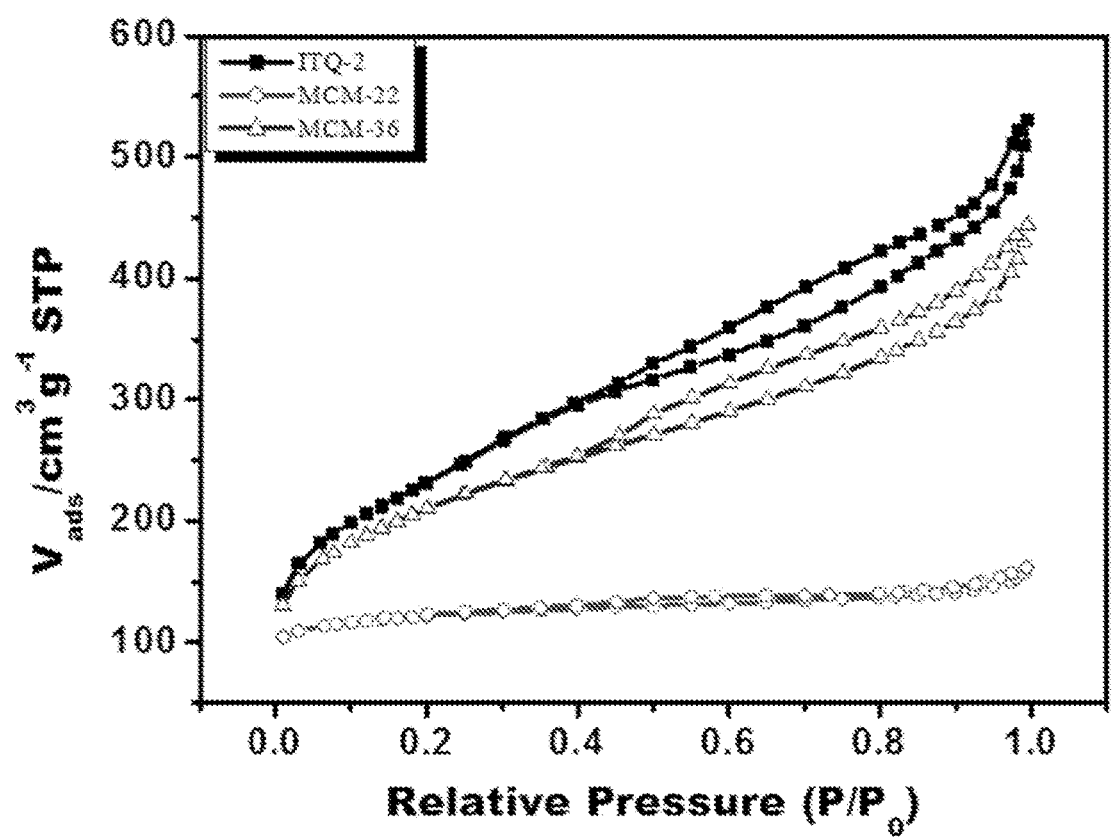
FIG. 2 represents adsorption-desorption isotherms of a MWW zeolite (MCM-22), a pillared MWW zeolite (MCM-36), and a delaminated MWW zeolite (ITQ-2).
Figure 3:
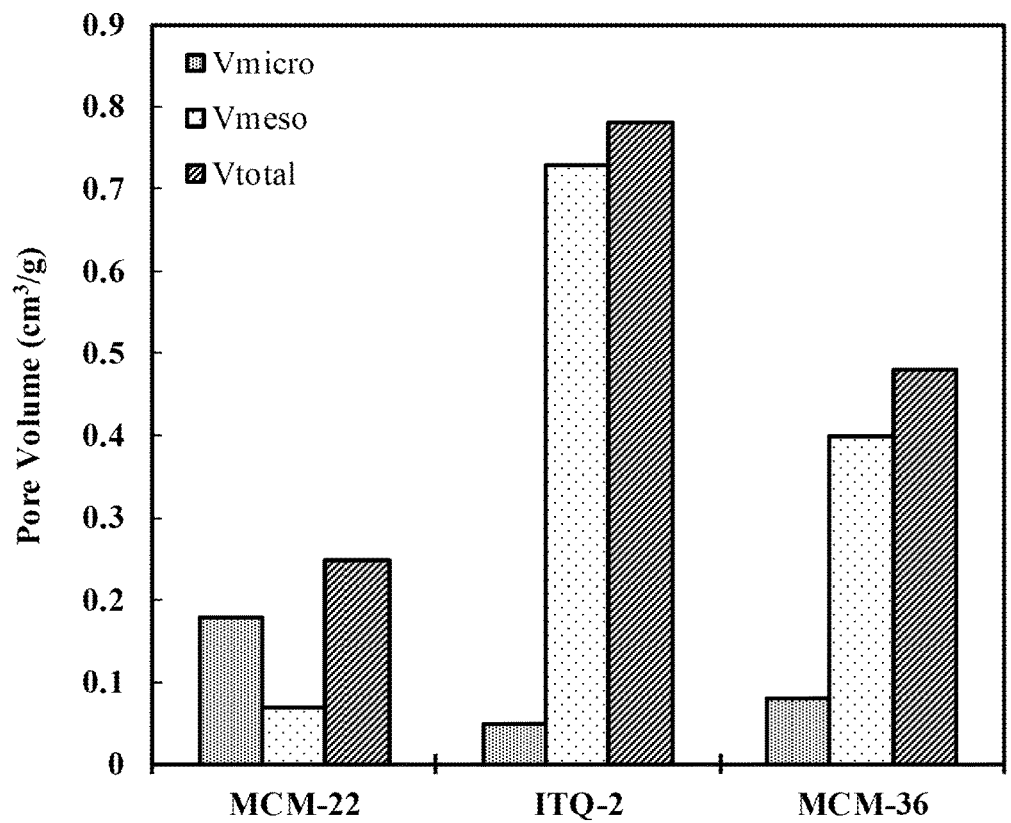
FIG. 3 represents a pore volume distribution of a MWW zeolite (MCM-22), a pillared MWW zeolite (MCM-36), and a delaminated MWW zeolite (ITQ-2).

Textural properties of the MWW zeolites, presented in Table 2, show bimodal pore system. There was a substantial increase in meso-pore volume due to delamination (ITQ-2) and pillarization (MCM-36) of MCM-22. This feature is also evident from adsorption-desorption isotherms (FIG. 2) and the plot showing pore volume distribution (FIG. 3).

TABLE 2

Textural properties of zeolites

| Zeolite Type | $V_{total}$ (cm$^3$/g) | $V_{meso}$ (cm$^3$/g) | $V_{micro}$ (cm$^3$/g) | $S_{BET}$ (m$^2$/g) | $S_{meso}$ (m$^2$/g) | $S_{micro}$ (m$^2$/g) | $D_p$ (nm) |
|---|---|---|---|---|---|---|---|
| MCM-22 | 0.25 | 0.07 | 0.18 | 468 | 79 | 389 | 4.9 |
| ITQ-2 | 0.78 | 0.73 | 0.05 | 773 | 656 | 117 | 7.8 |
| MCM-36 | 0.48 | 0.40 | 0.08 | 606 | 437 | 176 | 4.0 |
| MOR | 0.25 | 0.19 | 0.06 | 471 | 55 | 416 | 8.5 |

Ammonia TPD results (Table 3) indicate modest decrease in total acidity due to delamination (ITQ-2) and pillarization (MCM-36) of MCM-22. Despite having higher $SiO_2/Al_2O_3$ ratio, the MWW zeolites exhibited much higher acidity than MOR.

TABLE 3

Ammonia TPD results of zeolites

| Catalyst | Total acidity (mmol/g) | Amounts of $NH_3$ desorbed (mmol/g) | | |
|---|---|---|---|---|
| | | <650K | 650-820K | >820K |
| MCM-22 | 7.37 | — | 4.99 (658) | 2.38 (848) |
| ITQ-2 | 6.93 | 1.96 (603) | 1.59 (654) | 3.38 (828) |
| MCM-36 | 6.25 | 1.21 (610) | 4.63 (773) | 0.05 (873) |
| MOR | 4.93 | 0.30 (627) | 4.40 (786) | 0.30 (1017) |

Pt dispersion results for the metal-loaded MWW zeolites are presented in Table 4. All the impregnated mordenite catalysts (Pt/MOR) exhibited high platinum dispersion (>100%), while the ion-exchanged mordenite catalysts (Pt-MOR) showed lower dispersion (40-80%) of platinum.

TABLE 4

Dispersion of Pt in metal loaded zeolites

| Type | Sample ID | Dispersion |
|---|---|---|
| Pt Zeolites | 1Pt/MOR | 123% |
| | 2Pt/MOR | 104% |
| | 4Pt/MOR | 126% |
| | 4Pt-MOR | 40% |
| | 4Pt-M22 | 70% |

TABLE 4-continued

Dispersion of Pt in metal loaded zeolites

| Type | Sample ID | Dispersion |
|---|---|---|
| | 4Pt-IQ2 | 70% |
| Pt and Re Zeolites | 2Re/4Pt-M22 | Pt(70%) |
| | 2Re/2Pt-M22 | Pt(80%) |
| | 2Re/4Pt-IQ2 | Pt(70%) |
| | 2Re/2Pt-IQ2 | Pt(75%) |
| | 2Re/4Pt-M36 | Pt(70%) |

EXAMPLE 8

Table 5 lists the main reactions with mixtures of TMB, MEB and toluene over zeolite catalysts under the process conditions studied [S. Ali, M. Ali, K. Al-Nawad, C. Ercan, Y. Wang, Appl. Catal., A. 393 (1-2) 96-108; U. Al-Mubaiyedh, S. Ali, S. Al-Khattaf, Chem. Eng. Res. Des., 90 (11) 1943-1955]. Each reaction has been assigned an identification name for easy reference.

TABLE 5

Main reactions during the conversion of alkyl-aromatics

| Reaction No. | Reactants | Reaction | Products |
|---|---|---|---|
| De-1 | MEB | Dealkylation | Toluene + Ethane |
| Tr-1 | Toluene + TMB | Transalkylation | Xylene + Xylene |
| Tr-2 | Toluene + TMB | | Benzene + TeMB |
| Tr-3 | Toluene + MEB | | Xylene + Ethylbenzene |
| Tr-4 | Toluene + MEB | | Benzene + DMEB |
| Dp-1 | Toluene + Toluene | Disproportionation | Xylene + Benzene |
| Dp-2 | TMB + TMB | | Xylene + TeMB |
| Dp-3 | MEB + MEB | | Ethylbenzene + DMEB |

Abbreviations:
TMB = Trimethylbenzene;
MEB = Methylethylbenzene;
DMEB = Dimethylethylbenzene;
TeMB = Tetramethylbenzene Toluene formation occurs, mainly from dealkylation of MEBs (De-1), prior to the formation of xylenes. When the TMB+MEB feed is processed, in-situ production of toluene is required for the reactions (Tr-1 to Tr-4 and Dp-1) to proceed. The highly desirable reaction is the transalkylation of TMBs and toluene to produce two moles of xylenes (Tr-1). Xylene formation can also occur from disproportionation of toluene (Dp-1) or transalkylation of toluene and MEB (Tr-3). Disproportionation of TMB (Dp-2) is not desirable as it produces tetramethylbenzenes (TeMB). Heavy aromatics ($A_{10}$ and $A_{11}$) act as coke precursors and the reactions that produce them are not desirable. The reactions which form benzene and light hydrocarbons are also not preferred. Ethylbenzene formation reactions (Tr-3 and Dp-3) are also not desirable as the boiling point of ethylbenzene (136° C.) is too close to that of xylenes, especially p-xylene (138° C.). The parallel and consecutive reaction network is also characterized by multiple chemical equilibria, including isomerization of xylenes, TMBs and MEBs.

Performance evaluation results of catalysts obtained with Feed A are presented in Table 6 (350° C.) and Table 7 (400° C.). The product compositions as well as the conversion of MEBs, TMBs and $C_9$ aromatics are presented in these tables. The xylenes selectivity was calculated from the total xylenes yield and the conversion of $C_9$ aromatics. Xylenes yield at 350 and 400° C. over Pt zeolites and RePt zeolites is presented in FIG. 4 for comparison.

TABLE 6

Catalyst performance of MOR and MWW zeolites at 350° C.

| Catalyst | Product Composition (wt. %) | | | | | | | Conversion (wt. %) | | | Xylenes Selectivity (%) |
|---|---|---|---|---|---|---|---|---|---|---|---|
| | C1-C4 Alkanes | Benzene | Toluene | Xylenes | MEBs | TMBs | $C_{10}$ Aromatics | MEBs | TMBs | $C_9$ Aromatics | |
| Pt loaded catalysts | | | | | | | | | | | |
| 1Pt/MOR | 6.6 | 0.5 | 7.3 | 26.0 | 11.4 | 38.9 | 9.4 | 67.4 | 40.2 | 49.7 | 52.3 |
| 2Pt/MOR | 7.5 | 0.7 | 9.0 | 30.8 | 6.5 | 37.3 | 8.2 | 81.5 | 42.7 | 56.3 | 54.8 |
| 4Pt/MOR | 7.0 | 0.5 | 6.8 | 25.5 | 10.3 | 39.6 | 10.4 | 70.7 | 39.1 | 50.1 | 50.9 |
| 4Pt-MOR (IE) | 7.7 | 0.4 | 5.6 | 25.4 | 6.0 | 44.9 | 10.1 | 82.9 | 31.0 | 49.1 | 51.6 |
| 4Pt-M22 | 8.3 | 0.2 | 4.0 | 18.0 | 5.9 | 52.6 | 11.0 | 83.1 | 19.1 | 41.5 | 43.5 |
| 4Pt-IQ2 | 7.4 | 0.1 | 3.6 | 18.2 | 9.3 | 50.4 | 11.0 | 73.3 | 22.5 | 40.3 | 45.1 |
| Pt and Re loaded catalysts | | | | | | | | | | | |
| 2Re/2Pt-M22 | 7.3 | 0.1 | 4.8 | 9.0 | 8.6 | 59.6 | 10.6 | 75.4 | 8.3 | 31.8 | 28.5 |
| 2Re/4Pt-M22 | 7.7 | 0.2 | 3.6 | 16.3 | 7.1 | 54.5 | 10.6 | 79.8 | 16.2 | 38.5 | 42.4 |
| 2Re/2Pt-IQ2 | 7.2 | 0.1 | 3.4 | 15.0 | 10.9 | 53.8 | 9.5 | 68.9 | 17.3 | 35.4 | 42.6 |
| 2Re/4Pt-IQ2 | 7.6 | 0.1 | 4.0 | 15.9 | 9.9 | 53.1 | 9.3 | 71.6 | 18.3 | 37.0 | 43.2 |
| 2Re/4Pt-M36 | 7.3 | 0.6 | 7.9 | 28.2 | 8.3 | 38.4 | 9.3 | 76.2 | 40.9 | 53.3 | 53.0 |

Reaction Conditions: Feed Composition: 124-TMB = 65 wt. % + 1,3-MEB = 35 wt. %
Temperature: 350° C.;
Pressure: 300 psi;
LHSV: 2.4 h$^{-1}$,
H$_2$ flow rate: 50 ml/min

TABLE 7

Catalyst performance of MOR and MWW catalysts at 400° C.

| Catalyst | Product Composition (wt. %) | | | | | | | Conversion (wt. %) | | | Xylenes Selectivity (%) |
|---|---|---|---|---|---|---|---|---|---|---|---|
| | C1-C4 Alkanes | Benzene | Toluene | Xylenes | MEBs | TMBs | $C_{10}$ Aromatics | MEBs | TMBs | $C_9$ Aromatics | |
| H-MOR(20) | 2.1 | 1.2 | 10.9 | 26.6 | 6.9 | 32.0 | 8.8 | 76.0 | 48.8 | 59.1 | 45.0 |
| Pt loaded catalysts | | | | | | | | | | | |
| 1Pt/MOR | 9.6 | 0.9 | 9.9 | 33.4 | 2.0 | 36.5 | 7.7 | 94.3 | 43.9 | 61.5 | 54.3 |
| 2Pt/MOR | 8.1 | 1.4 | 13.3 | 36.9 | 1.9 | 33.1 | 5.3 | 94.5 | 49.1 | 65.0 | 56.8 |
| 4Pt/MOR | 8.0 | 1.1 | 11.6 | 34.4 | 3.1 | 35.6 | 6.2 | 91.1 | 45.2 | 61.3 | 56.1 |
| 4Pt-MOR (IE) | 8.2 | 1.2 | 11.7 | 34.2 | 1.7 | 37.2 | 5.9 | 95.3 | 42.8 | 61.2 | 55.9 |
| 4Pt-M22 | 8.3 | 0.7 | 10.1 | 29.2 | 1.7 | 42.4 | 7.5 | 95.2 | 34.7 | 55.9 | 52.2 |
| 4Pt-IQ2 | 7.8 | 0.6 | 10.0 | 27.8 | 4.8 | 40.8 | 8.3 | 86.3 | 37.2 | 54.4 | 51.0 |
| Pt and Re loaded catalysts | | | | | | | | | | | |
| 2Re/2Pt-M22 | 7.3 | 0.5 | 10.3 | 24.2 | 5.4 | 45.0 | 7.4 | 84.6 | 30.8 | 49.6 | 48.7 |
| 2Re/4Pt-M22 | 7.3 | 0.7 | 9.7 | 26.7 | 5.3 | 42.5 | 7.8 | 84.9 | 34.7 | 52.3 | 51.1 |
| 2Re/2Pt-IQ2 | 7.3 | 0.5 | 9.1 | 25.0 | 6.3 | 42.4 | 9.3 | 81.9 | 34.8 | 51.3 | 48.8 |
| 2Re/4Pt-IQ2 | 7.7 | 0.5 | 9.8 | 25.9 | 5.5 | 41.8 | 8.8 | 84.3 | 35.7 | 52.7 | 49.2 |
| 2Re/4Pt-M36 | 8.0 | 1.2 | 11.8 | 35.7 | 2.3 | 34.8 | 6.1 | 93.4 | 46.5 | 62.9 | 56.8 |

Reaction Conditions: Feed Composition: 124-TMB = 65 wt. % + 1,3-MEB = 35 wt. %
Temperature: 400° C.;
Pressure: 300 psi;
LHSV: 2.4 h$^{-1}$;
H$_2$ flow rate: 50 ml/min

EXAMPLE 9

Comparison of results obtained by H-MOR and Pt-loaded MOR catalysts (Table 7) clearly shows promotion of dealkylation of MEB by incorporation of Pt metal. The MEB conversion increased from 76 wt. % to 91-95 wt. %. The increase in MEB dealkylation resulted in the formation of more toluene, which in turn led to significant increase in xylene yield from about 27 wt. % from H-MOR to 33-37 wt. % for Pt/MOR catalysts. It can also be observed that the amount of $C_{10}$ aromatics was also lower in products obtained over Pt/MOR catalysts, which could be due to higher dealkylation of $C_{10}$ aromatics—especially DMEBs. A significant improvement in xylenes selectivity (from 45% to 54-57%) due to Pt loading of H-MOR was also observed. The addition of metal also improves the catalytic stability of zeolite and extends the cycle length [T. C. Tsai, S. B. Liu, I. Wang, Catal. Surv. Asia 13 (2009) 94-103]. Hence, an overall improvement in catalytic performance was attributed to the addition of metal function.

EXAMPLE 10

Comparison of results obtained by 4Pt/MOR (impregnated) and 4Pt-MOR (ion-exchanged catalysts (Tables 6 and 7) shows that 4Pt-MOR (ion-exchanged) is more active for MEB conversion than 4Pt/MOR (impregnated) due to Pt function. Pt incorporation by ion-exchange method is facilitated by the exchange of cationic Pt complexes with protons located predominantly in the intracrystalline pores. On the other hand, the impregnation method invokes anionic Pt complexes and hence the Pt is located mostly in extracrystalline surfaces of the zeolite. It should be noted that the impregnated mordenite (Pt/MOR) exhibited high Pt dispersion exceeding 100%, while the 4Pt-MOR showed Pt dispersion of only 40% (Table 4). In a previous study it was reported that Pt/MOR had lower dispersion (larger metal particle) but was more active in hydrogenation than the ion-exchanged one (Pt-MOR) [T. C. Tsai, W. H. Chen, S. B. Liu, C. H. Tsai, I. Wang, Catal. Today 73 (2002) 39-47]. The higher MEB conversion over 4Pt-MOR could be attributed to its stronger Pt activity despite lower dispersion.

EXAMPLE 11

The addition of Re into the Pt ion exchanged zeolite did not change the particle dispersion and size (Table 4). Re/Pt-zeolite exhibited less MEB conversion than Pt-zeolite, indicating that Re inhibited the hydrogenation activity of Pt (Tables 6 and 7). Although the yields of all by-products could not be determined, Pt/zeolite should catalyze high naphthenic product yield and low benzene purity. Since Pt is known to have higher hydrogenation activity than Re. Hence, addition of Re into Pt/zeolite may suppress the hydrogenation activity of Re. The reduced MEB conversion over Re/Pt-zeolite may be attributed to the reduced hydrogenation activity by Re component. Reduction in TMB conversion was not significant. These effects, however, resulted in reduction of xylenes yield 3-4 wt. %.

EXAMPLE 12

Modernite and MCM-36 exhibited higher transalkylation activity than MCM-22 and ITQ-2, indicating by higher xylene yield, reduced $A_{10}$ yield and enhanced TMB conversion (Tables 6 and 7). It can be noticed that TMB conversion is directly associated with acid catalysis and little affected by metal catalysis. On the other hand, MEB conversion is strongly associated with metal catalysis.

MCM-22 and ITQ-2 exhibited lower TMB yield, which may be due to low diffusivity of TMB through the 10-MR pore system. It is known that 10-MR zeolites such as MFI had low TMB conversion [S. A. Ali, K. Ogunronbi, S. Al-Khattaf, Chem. Engg. Res. Des., 91 (2013) 2601-2616]. TMB conversion over MCM-22 was enhanced by introduction of mesoporosity by pillaring in MCM-36. The high MEB conversion over Pt/MCM-22 and Pt/ITQ-2 could be attributed to metal function, indicating that metal could be located in 12-MR or external surface. Thus Pt/MCM22 and Pt/ITQ-2 exhibited similar MEB conversion as Pt/MOR.

While alkyl-aromatic dealkylation is a monomolecular reaction, the transalkylation reactions require close interaction between two alkyl-aromatic molecules [J. M. Serra, E. Guillon, A. Corma, J. Catal., 225 (2004) 459-469; H. G. Karge, S. Ernst, M. Weihe, V. Weiss, J. Weitkamp, Stud. Surf. Sci. Catal. 84 (1994) 1805-1812]. This implies that an adsorbed and activated molecule on an acid site reacts with another adsorbed molecule to yield a biphenylic intermediate inside the zeolite channel system [S. Al-Khattaf, S. A. Ali, A. Aitani, N. ilková, D. Kubička, J. Čejka, Catalysis Reviews: Science and Engineering, 56 (2014) 333-402]. More specifically, in the TMB transalkylation, a secondary carbenium ion formed on the alkyl chain would be the alkylating agent to form a series of carbocations. In addition, in the case of reactions occurring in confined spaces, the type of biphenylic intermediate and the scission type will also be determined by the size and geometry of the intrazeolitic pores in which the reaction occurs. The sizes of the intermediates involved in transalkylation reactions are much larger than the one involved in dealkylation. Therefore, the zeolite pore topology determines the selectivity to transalkylation versus dealkylation reactions by restricting the formation of bulkier transition states.

EXAMPLE 13

Blending 10 wt. % toluene in 60 wt. % TMB and 30 wt. % MEB feed acted as an inhibitor in transalkylation (reduced TMB conversion) and dealkylation (reduced MEB conversion) as shown in Table 8. The inhibition effect in terms of xylene yield was significant (5-10 wt. %) over MCM-22 and ITQ-2, while it was modest (1-2 wt. %) for 4Pt/MOR and MCM-36. Only in case of 4Pt-MOR(IE), slight improvement in MEB and TMB conversion as well as xylene yield was observed.

TABLE 8

Effect of toluene addition on the performance of MOR and MWW catalysts at 400° C.

| Catalysts | MEB Conversion (wt. %) | | TMB Conversion (wt. %) | | Xylenes Yield (wt. %) | |
|---|---|---|---|---|---|---|
| | Feed A* | Feed B** | Feed A* | Feed B** | Feed A* | Feed B** |
| 4Pt/MOR | 91.1 | 87.4 | 45.2 | 43.7 | 34.4 | 32.8 |
| 4Pt-MOR (IE) | 95.3 | 96.8 | 42.8 | 44.7 | 34.2 | 35.8 |
| 4Pt-M22 | 95.2 | 87.1 | 34.7 | 30.6 | 29.2 | 24.3 |
| 4Pt-IQ2 | 86.3 | 74.3 | 37.2 | 30.7 | 27.8 | 21.9 |
| 2Re/4Pt-M22 | 85.0 | 72.6 | 34.7 | 25.9 | 26.7 | 18.7 |
| 2Re/4Pt-IQ2 | 84.3 | 59.1 | 35.7 | 25.8 | 25.9 | 16.1 |
| 2Re/4Pt-M36 | 93.4 | 89.6 | 46.5 | 44.5 | 35.7 | 33.7 |

*Feed A (wt. %): TMB (65) + MEB (35)
**Feed B (wt. %): TMB (60) + MEB (30) + Toluene (10)

This result indicates that when the rate of MEBs dealkylation is high enough, adding toluene to heavy reformate does not increase of the xylenes yields, because sufficient toluene for TMB conversion is already available. In the exceptional case of 4Pt-MOR(IE), it seems that the high MEB dealkylation activity is maintained, despite the presence of toluene, due to strong Pt activity. In addition, the TMB conversion was also high resulting in 1.6 wt % increase in xylene yield.

The thermodynamic equilibrium value of xylene yield depends on the M/R ratio of the feed [T. C. Tsai, S. B. Liu, I. Wang, Catal. Surv. Asia 13 (2009) 94-103; J. M. Serra, E. Guillon, A. Corma, J. Catal. 232 (2005) 342-354]. Since the M/R ratio of feed B was less than feed A, the thermodynamic equilibrium value of xylene yield is also lower. The results indicate excessive presence of toluene precursor (MEBs) and toluene do not help in increasing the xylene yield.

The invention claimed is:

1. A process for converting an alkyl-aromatic hydrocarbon stream to a BTX-rich stream, comprising:
    contacting the alkyl-aromatic hydrocarbon stream with a zeolite catalyst in the presence of hydrogen gas at a temperature in a range of 200-500° C. and at a pressure in a range of 1-3 MPa to form a product stream, wherein a molar ratio of the hydrogen gas to hydrocarbon compounds in the alkyl-aromatic hydrocarbon stream is in the range of 1:1-6:1, and wherein the zeolite catalyst comprises:
    a pillared MWW zeolite, and
    at least two metals selected from the group consisting of Pt, Re, Mo, and Ni, and
    wherein the zeolite catalyst comprises micro-pores having a specific pore volume in the range of 0.05-0.1 cm$^3$/g, and meso-pores having a specific pore volume in the range of 0.3-0.5 cm$^3$/g; and
    separating $C_{5-}$ and $C_{9+}$ hydrocarbon compounds from the product stream to form the BTX-rich stream.

2. The process of claim 1, further comprising:
    treating the zeolite catalyst with the hydrogen gas in a temperature range of 250-450 ° C. prior to the contacting.

3. The process of claim 1, wherein at least 50% by weight of the BTX-rich stream is xylene and the process further comprises separating xylene from the BTX-rich stream.

4. The process of claim 1, wherein the alkyl-aromatic hydrocarbon stream comprises $C_{9+}$ alkyl-aromatic hydrocarbon compounds.

5. The process of claim 1, wherein the alkyl-aromatic hydrocarbon stream has a space velocity in the range of 1-5 h$^{-1}$.

6. The process of claim 1, wherein the alkyl-aromatic hydrocarbon stream comprises toluene and one or more of methylethylbenzene, trimethylbenzene, dimethylethylbenzene, and tetramethylbenzene, and the process further comprises reducing a toluene content of the alkyl-aromatic hydrocarbon stream in a separation unit prior to the contacting.

7. The process of claim 6, wherein the alkyl-aromatic hydrocarbon stream has an average methyl-to-benzene molar ratio in the range of 2-2.5 prior to the contacting.

8. The process of claim 1, wherein the zeolite catalyst comprises 0.1-1 wt % Pt and 0.1-1 wt % Re.

9. The process of claim 1, wherein the pillared MWW zeolite comprises silica pillars.

* * * * *